United States Patent [19]

Yanaki

[11] Patent Number: 4,763,343
[45] Date of Patent: Aug. 9, 1988

[54] METHOD AND STRUCTURE FOR OPTIMIZING RADIOGRAPHIC QUALITY BY CONTROLLING X-RAY TUBE VOLTAGE, CURRENT, FOCAL SPOT SIZE AND EXPOSURE TIME

[76] Inventor: Nicola E. Yanaki, 6199 Dunn Ave., San Jose, Calif. 95123

[21] Appl. No.: 910,496

[22] Filed: Sep. 23, 1986

[51] Int. Cl.$^4$ .............................................. H05G 1/34
[52] U.S. Cl. ................................... 378/110; 378/112; 378/113; 378/95
[58] Field of Search ................. 378/110, 112, 113, 95, 378/37, 207

[56] References Cited

U.S. PATENT DOCUMENTS

| | | | |
|---|---|---|---|
| 3,894,235 | 7/1975 | Franke | 378/112 |
| 4,075,484 | 2/1978 | Meyer-Ebrecht et al. | 378/207 |
| 4,090,084 | 5/1978 | Epstein et al. | 378/37 |
| 4,160,906 | 7/1979 | Daniels et al. | 378/118 |
| 4,400,823 | 8/1983 | Haendle | 378/113 |
| 4,638,500 | 1/1987 | Smits et al. | 378/207 |

*Primary Examiner*—Janice A. Howell
*Assistant Examiner*—David P. Porta
*Attorney, Agent, or Firm*—Alan H. MacPherson; Thomas S. MacDonald; Edel M. Young

[57] ABSTRACT

A structure and method for providing optimum recording of X-ray images without need for experimenting to learn optimum X-ray tube voltage, current, anode focal spot size and exposure time. The method and structure of this invention sample the radiation passed through an object to be radiographed during a short portion of the total exposure time and adjust voltage, current and focal spot size so that the radiation delivered by the X-ray tube during the remainder of the exposure time will produce optimum contrast between structures within the object being radiographed, also optimum sharpness of the image and optimum darkening of a film, xerographic picture, fluoroscopic image, or other recording medium. The method and structure of this invention account for variations in absorption coefficient between one object to be radiographed and the next. This invention is particularly useful for medical applications, and in the medical field, particularly important in mammography.

34 Claims, 13 Drawing Sheets

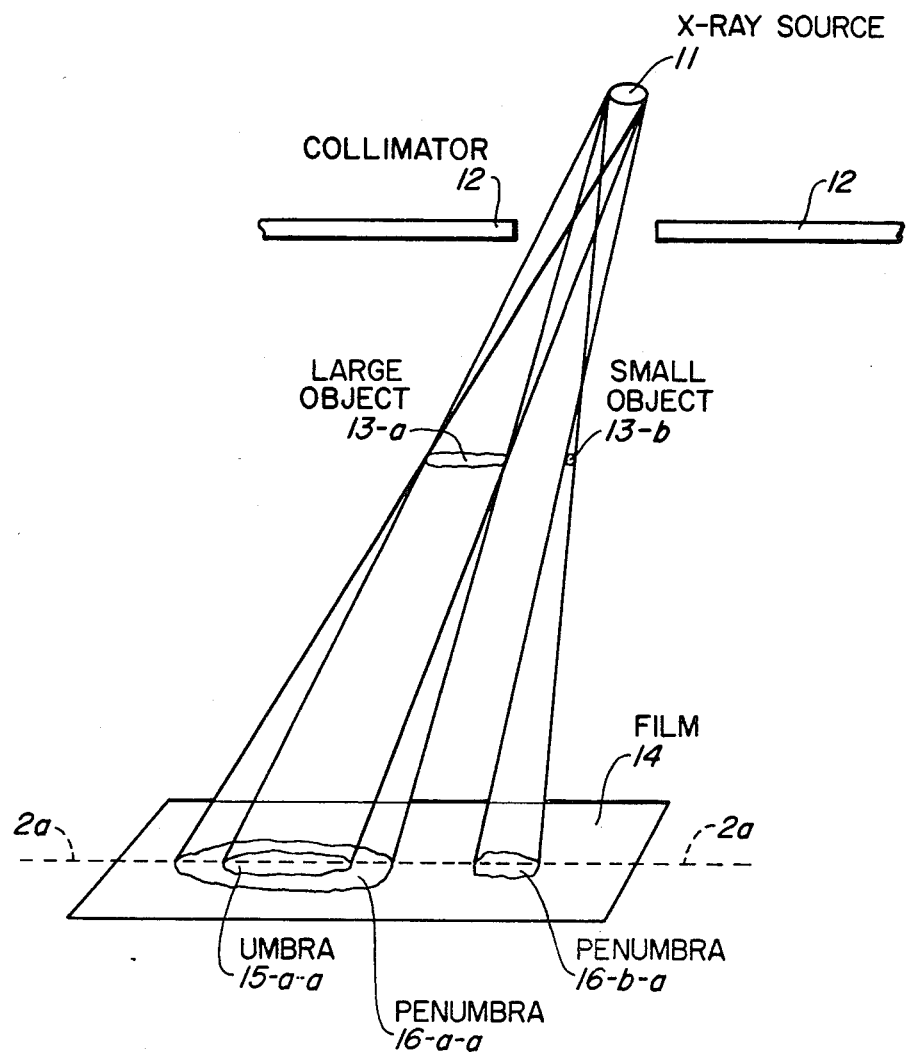
FIG._1a. (PRIOR ART)

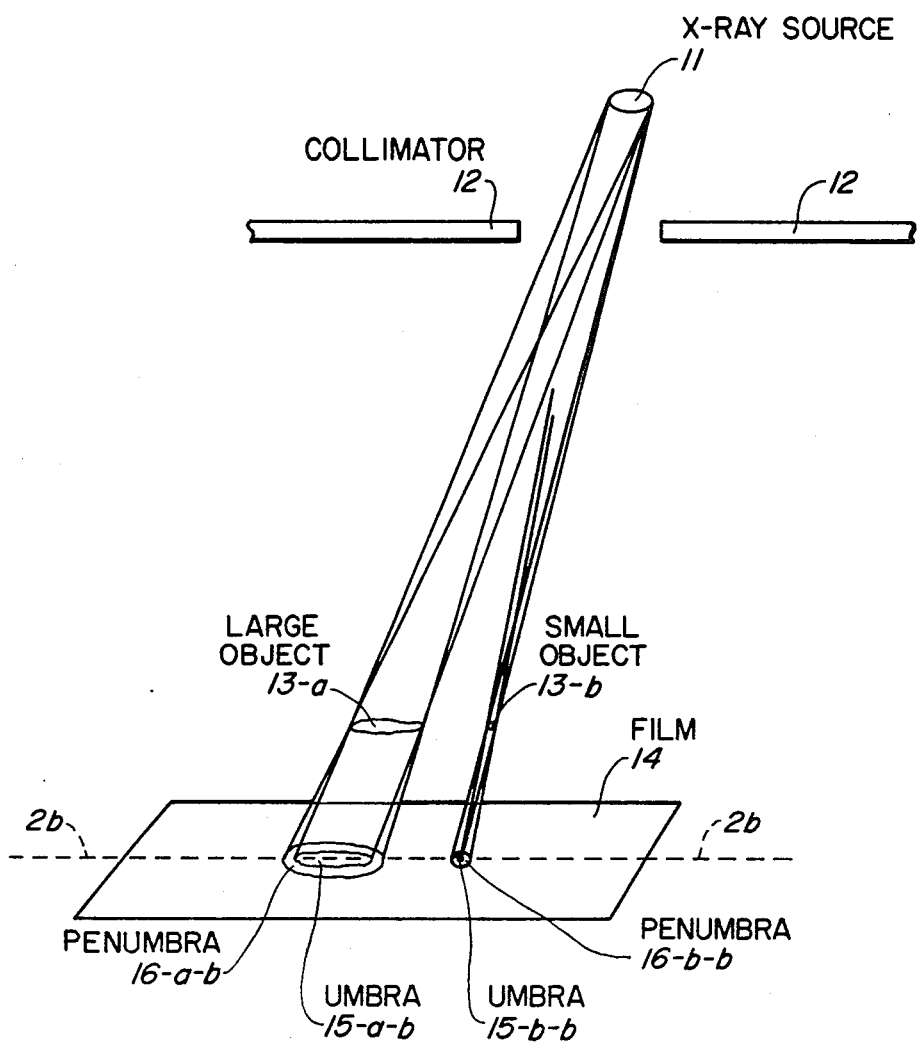
FIG._1b. (PRIOR ART)

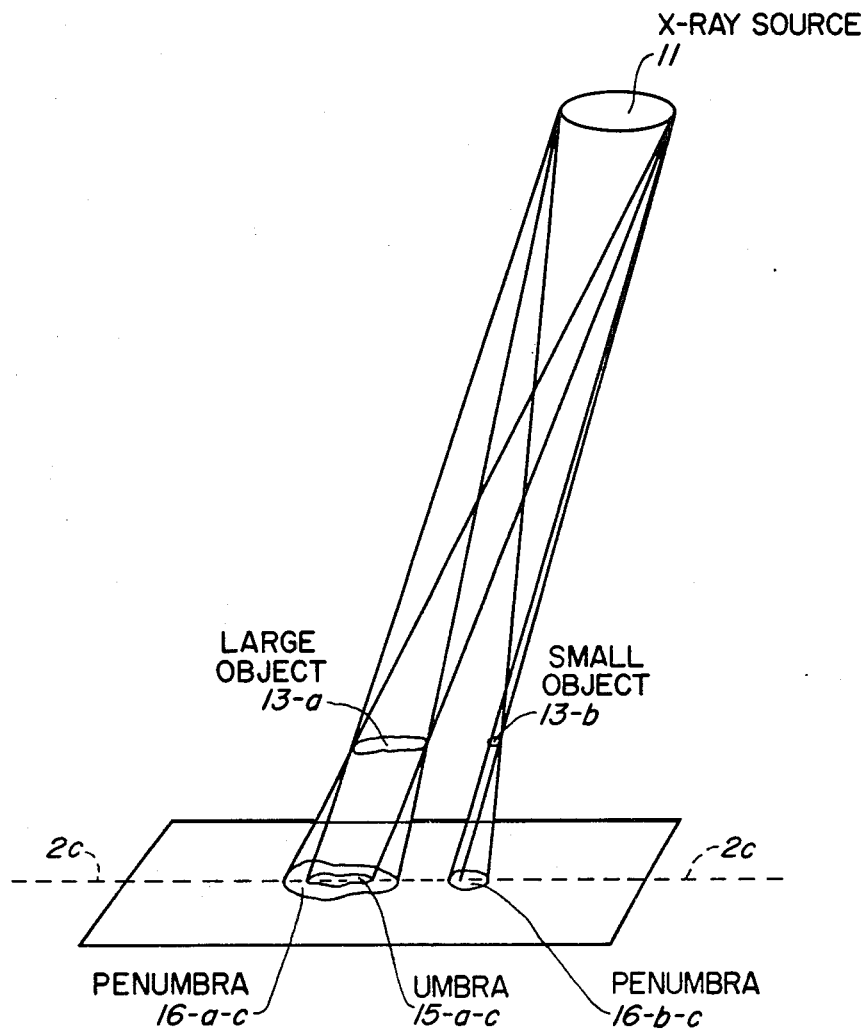
FIG._1c. (PRIOR ART)

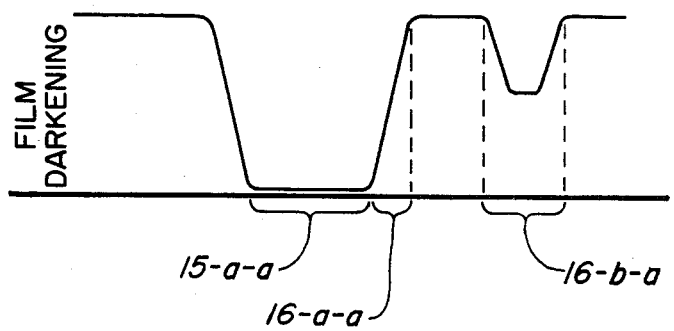
FIG._2a. (PRIOR ART)
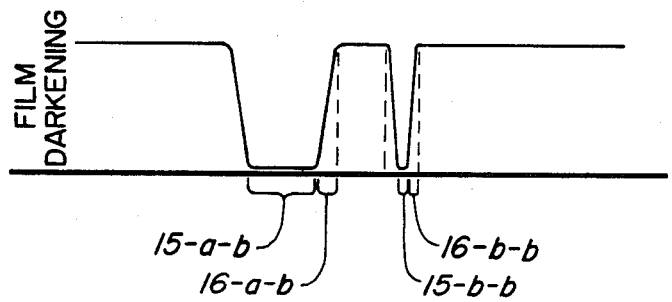
FIG._2b. (PRIOR ART)
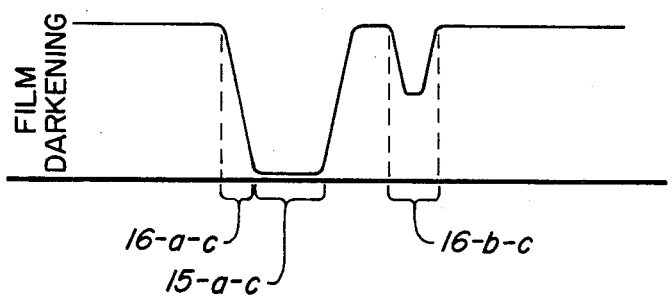
FIG._2c. (PRIOR ART)

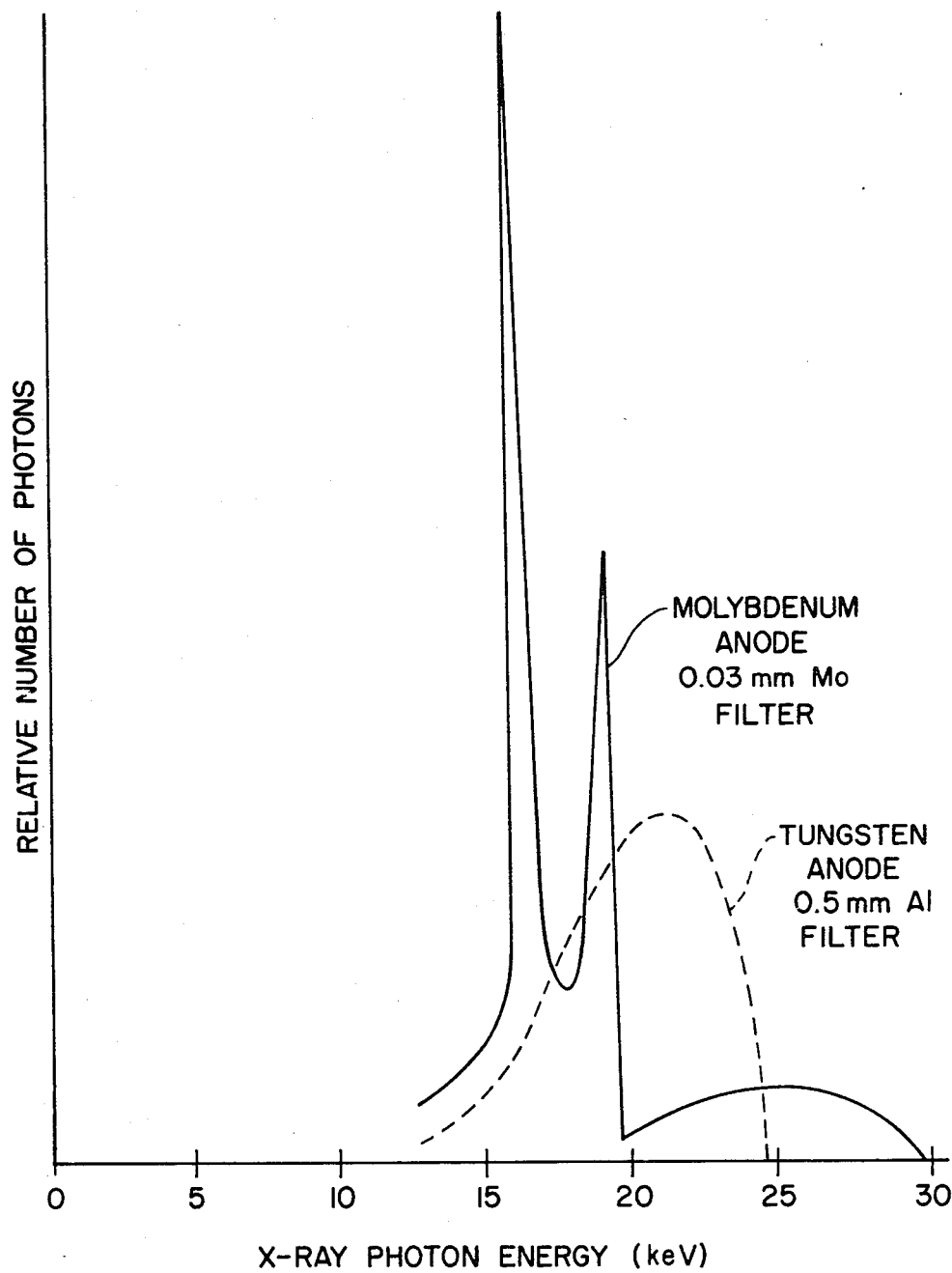
FIG._3. (PRIOR ART)

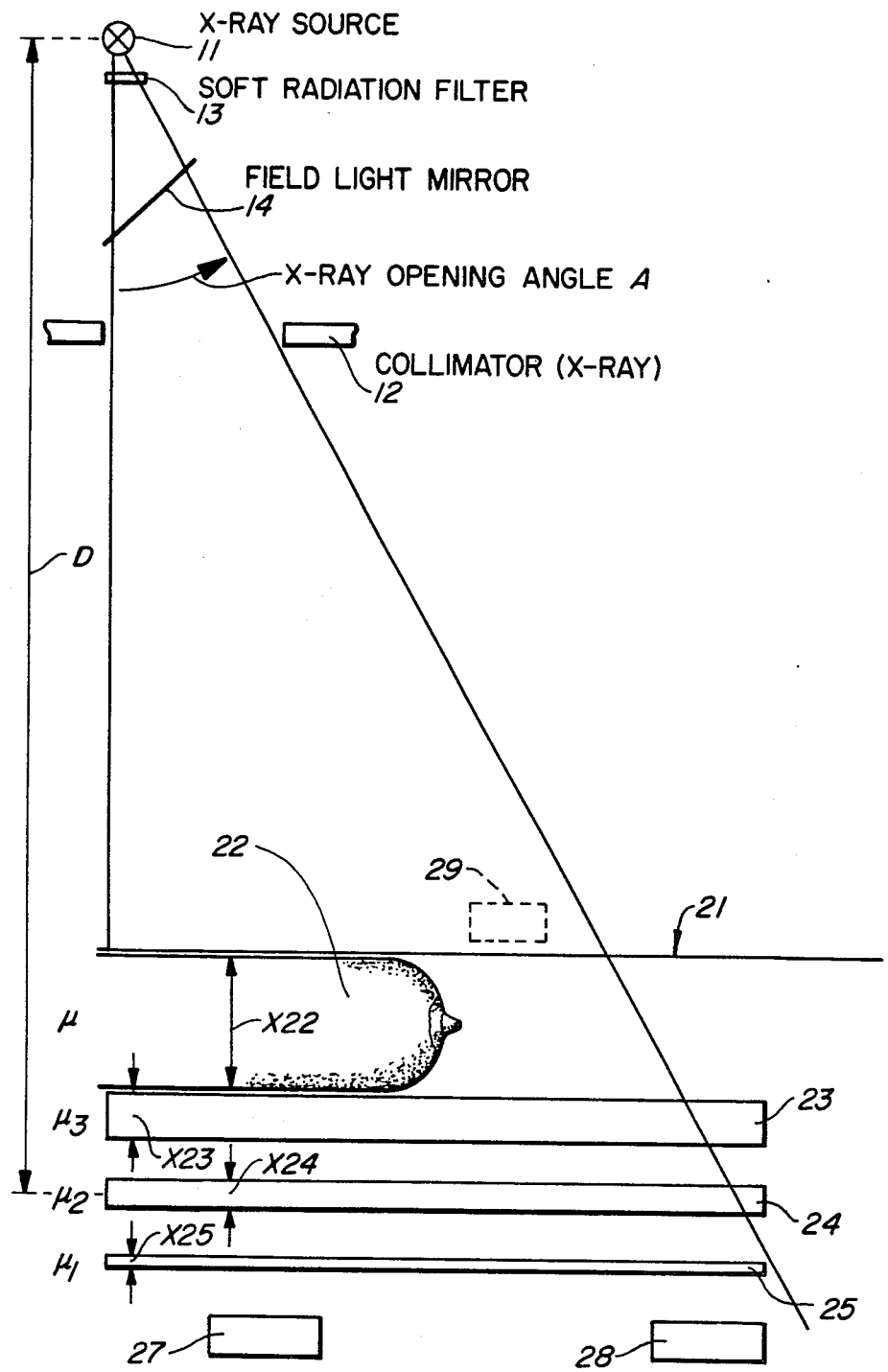
FIG._4.

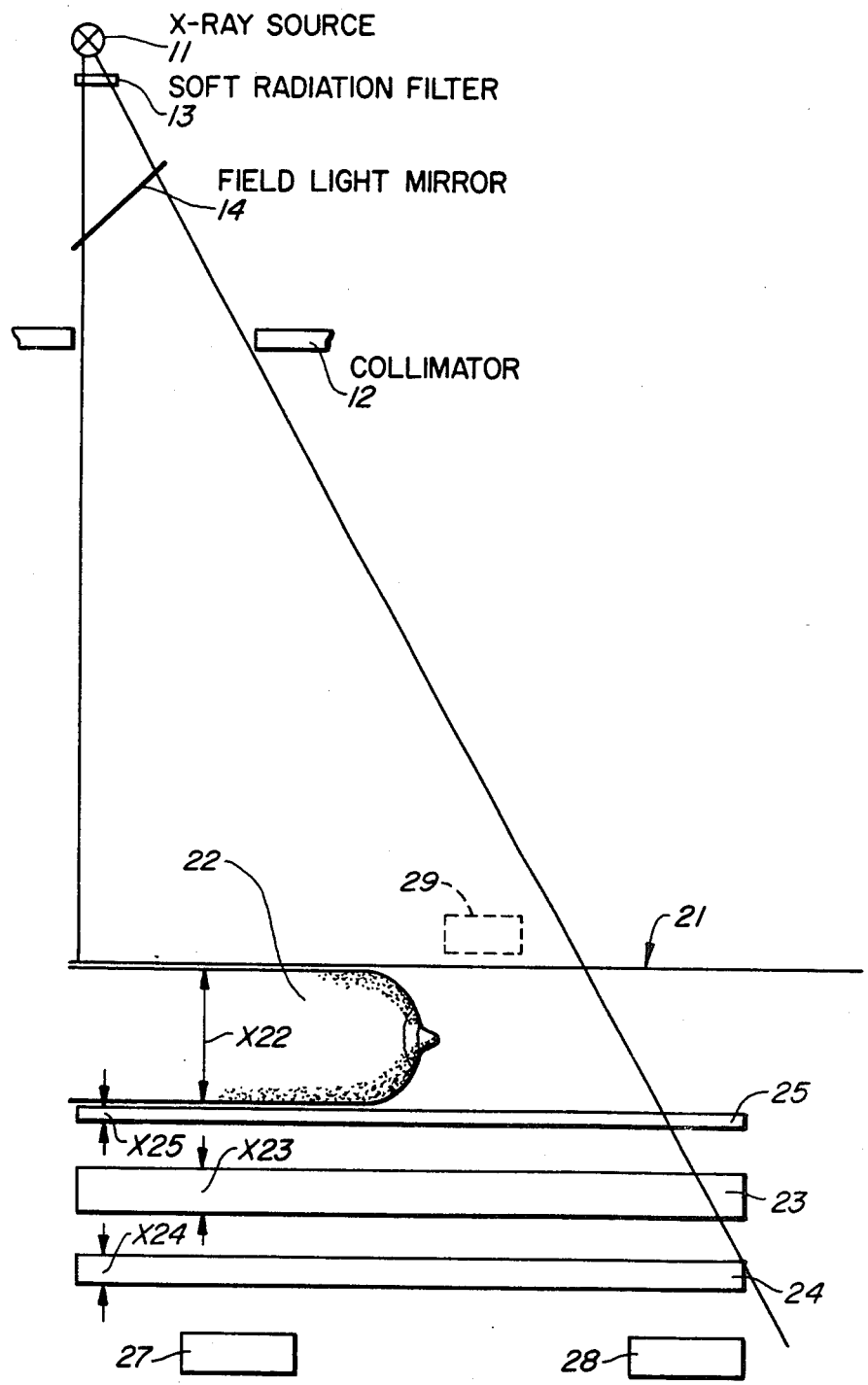
FIG._5.

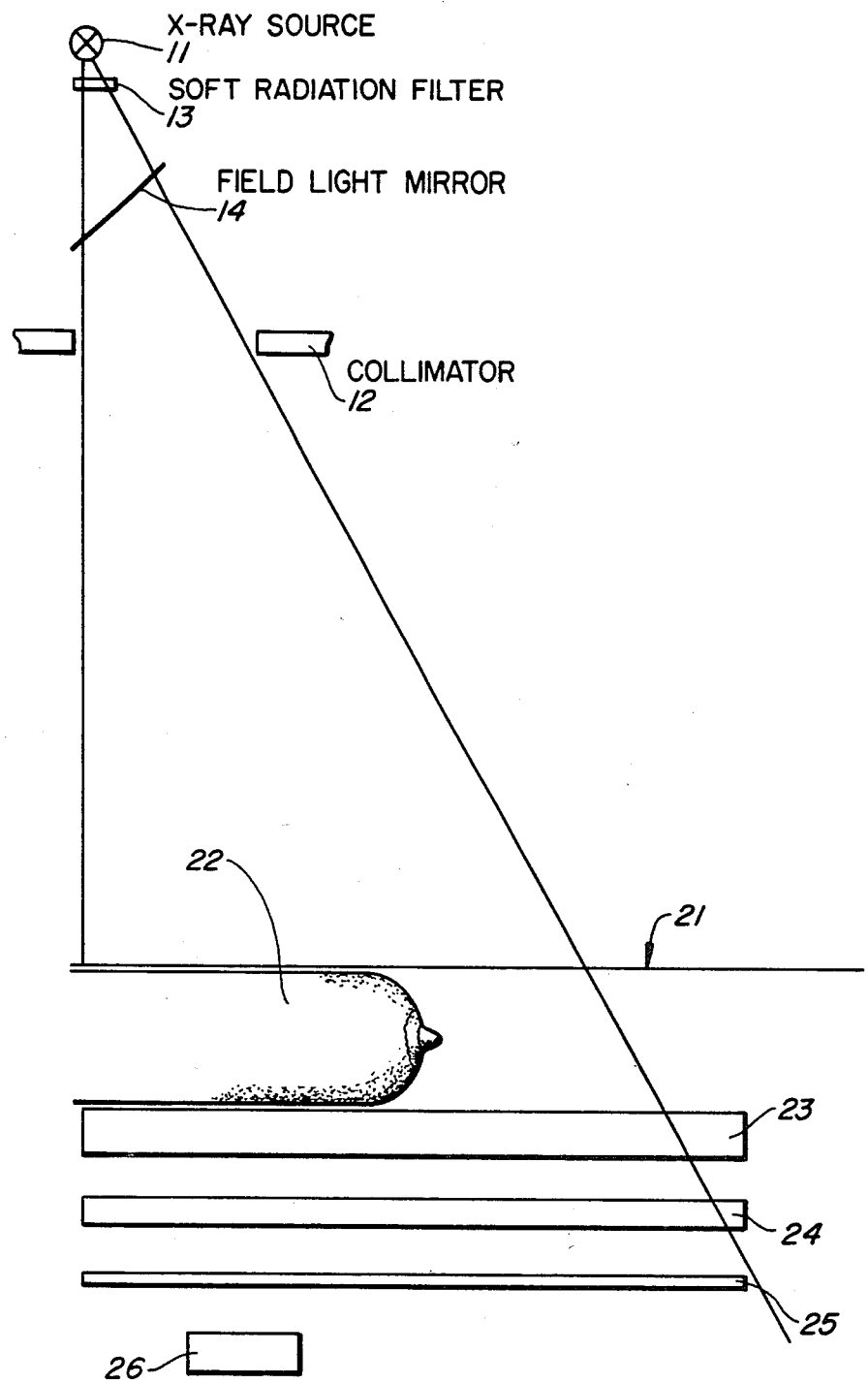
FIG._6.

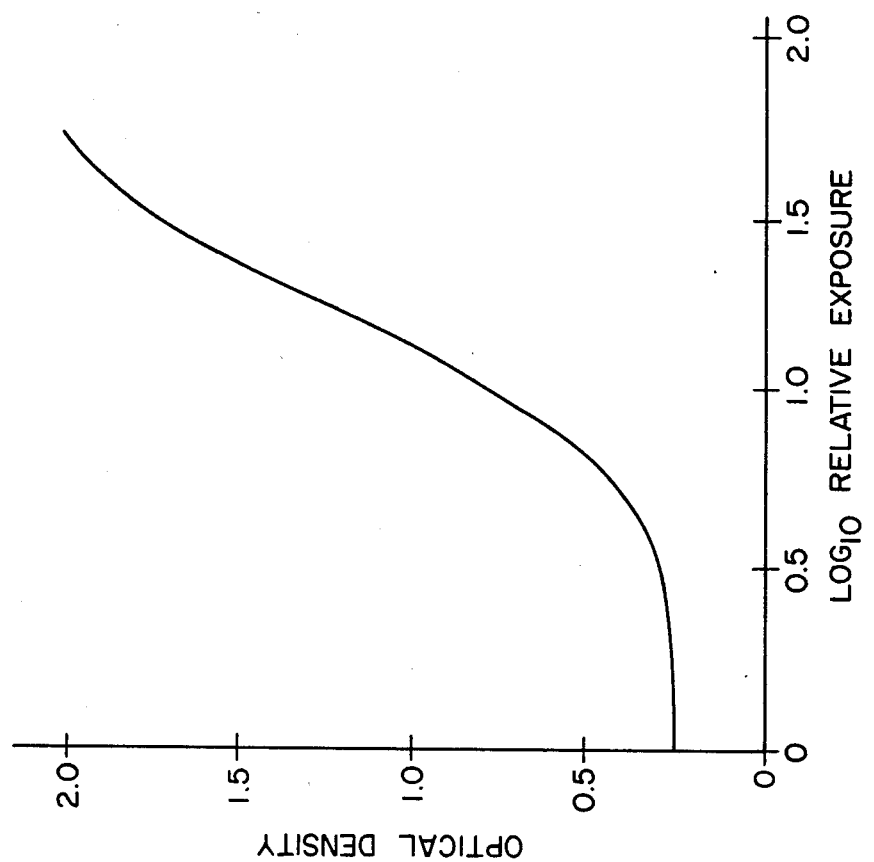
FIG._10.
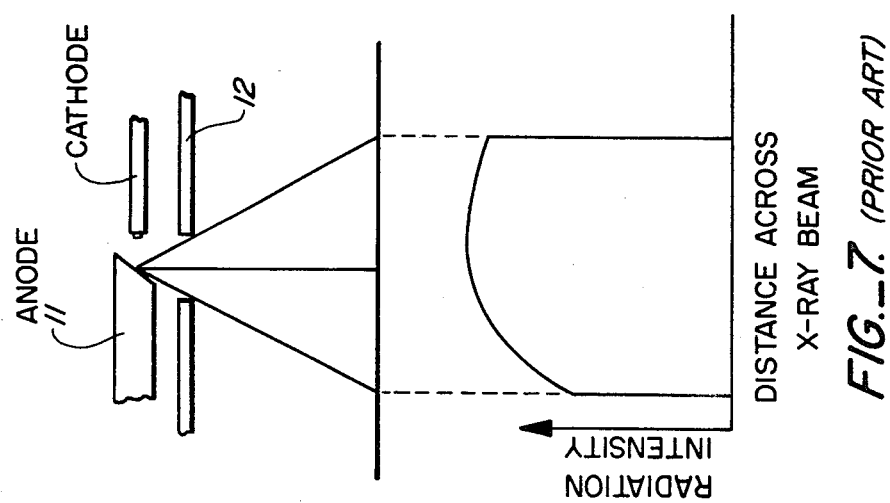
FIG._7. (PRIOR ART)

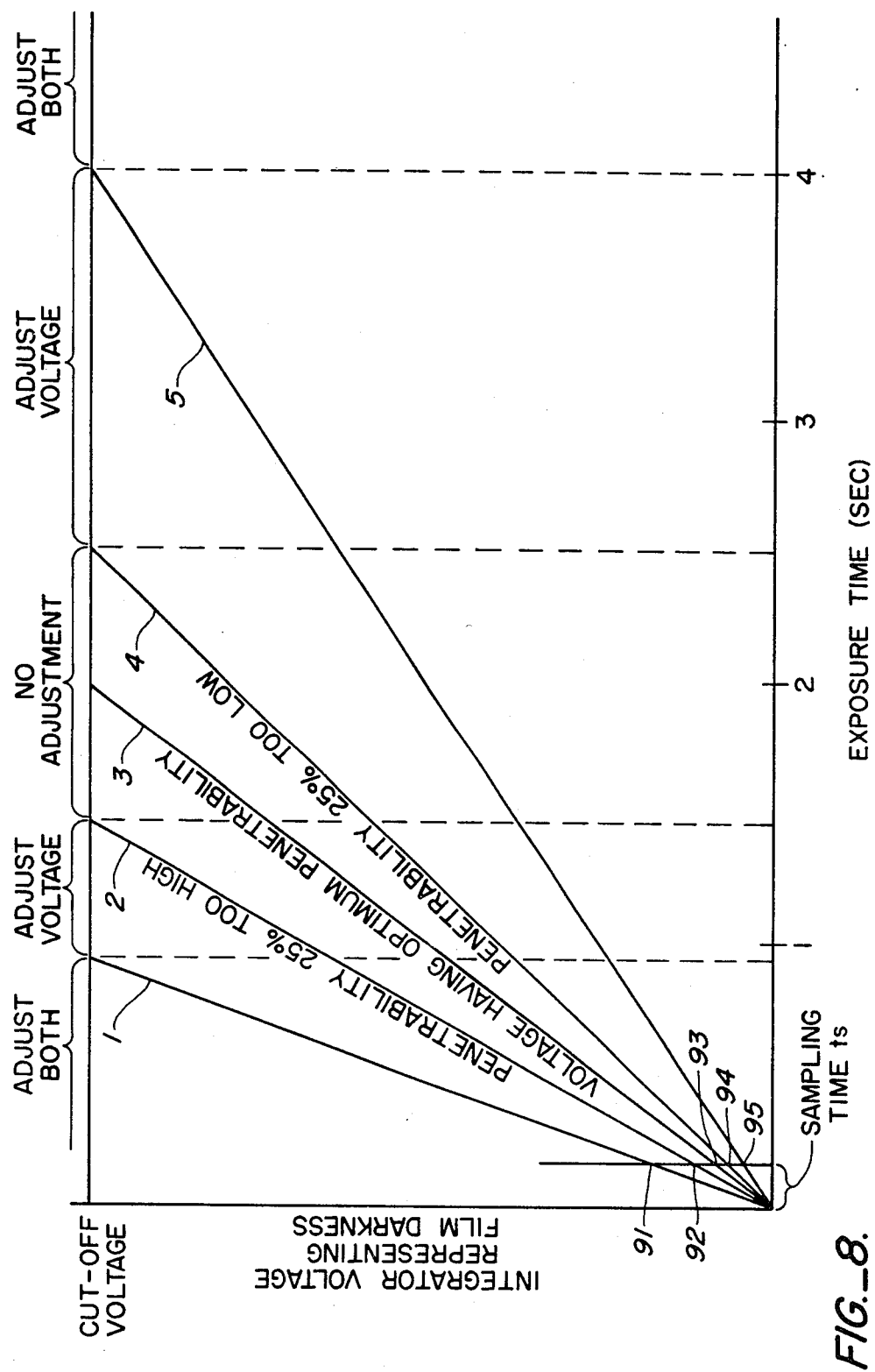
FIG._8.

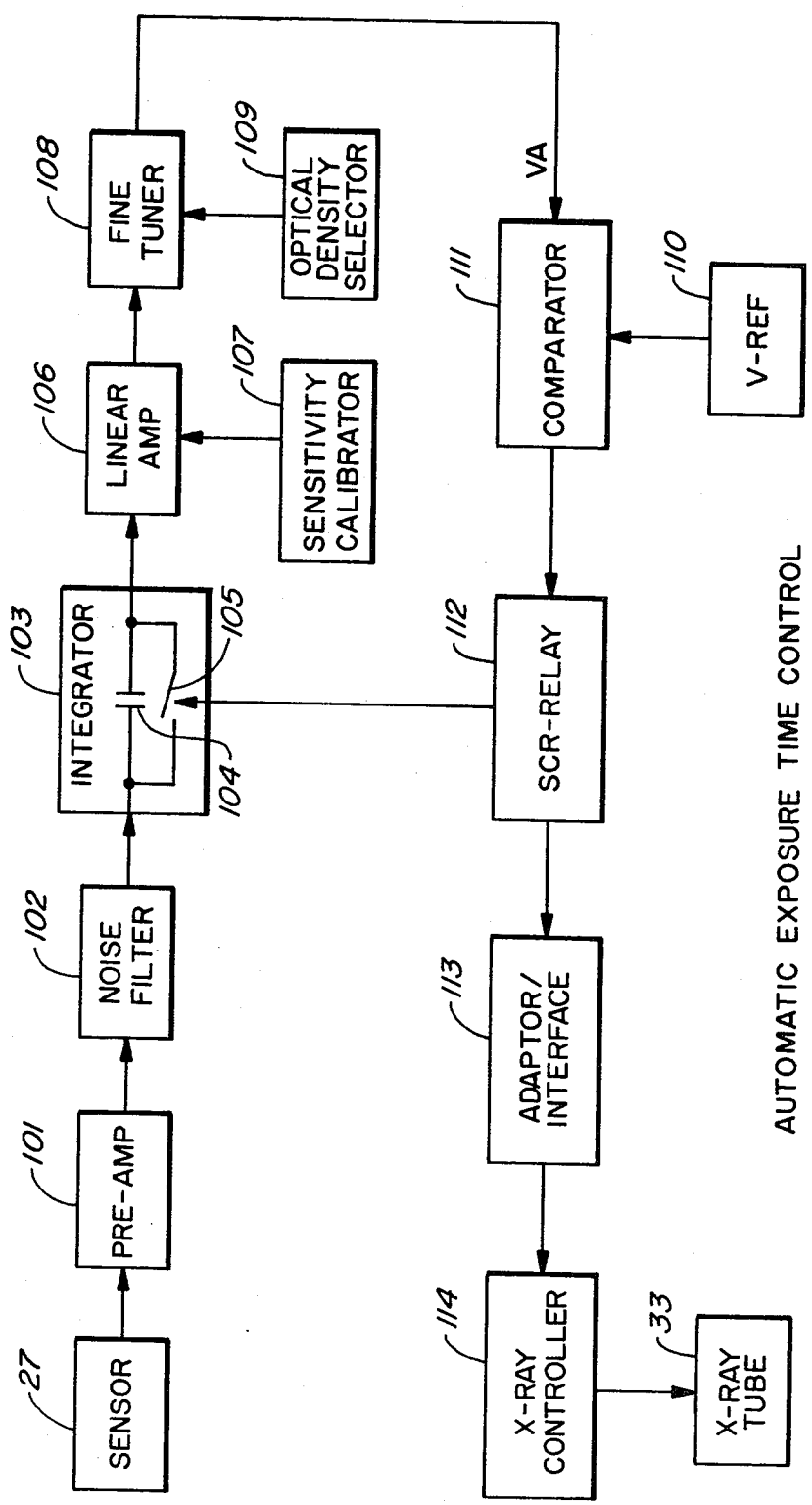
FIG._9. (PRIOR ART)
AUTOMATIC EXPOSURE TIME CONTROL

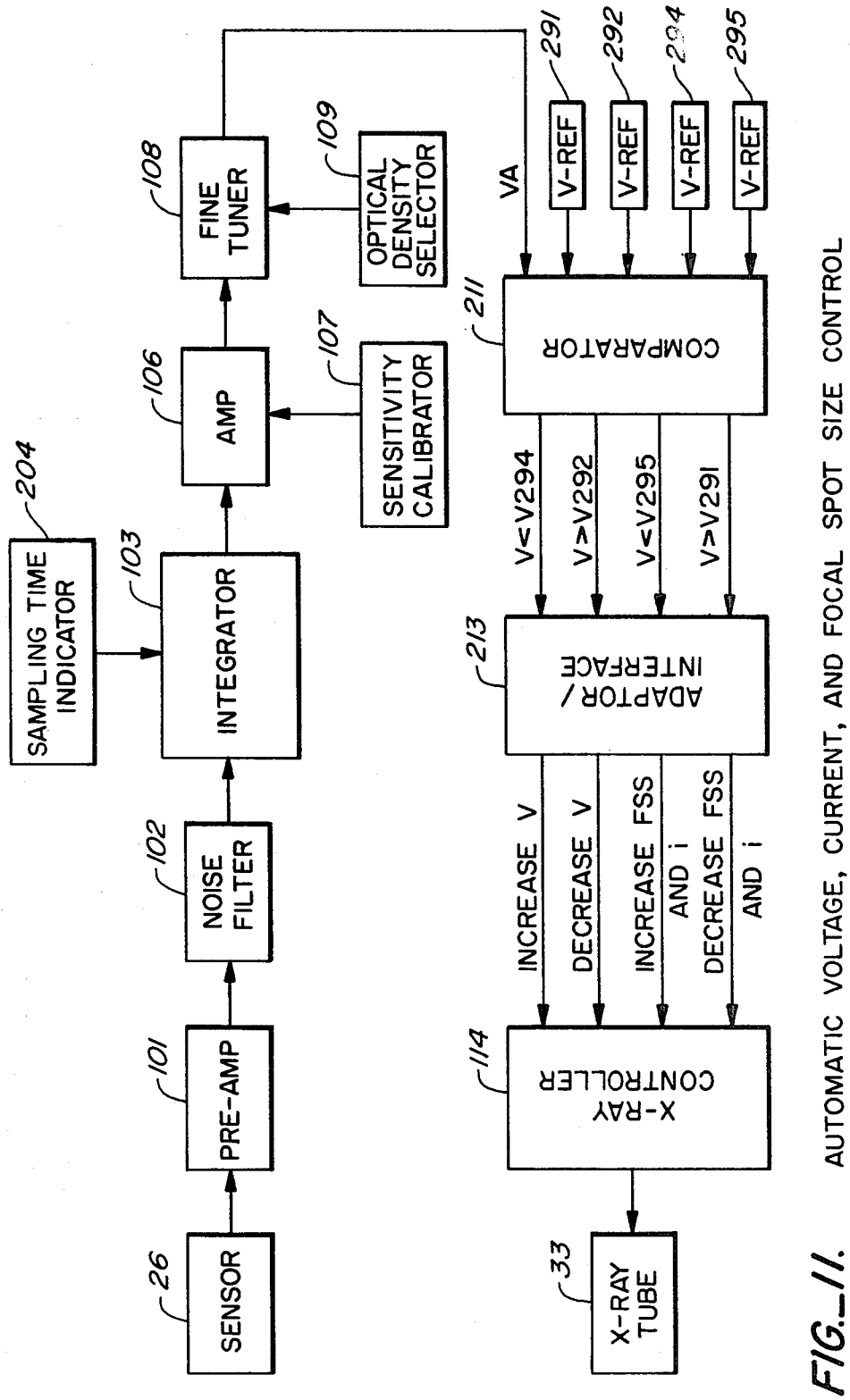
FIG._11. AUTOMATIC VOLTAGE, CURRENT, AND FOCAL SPOT SIZE CONTROL.

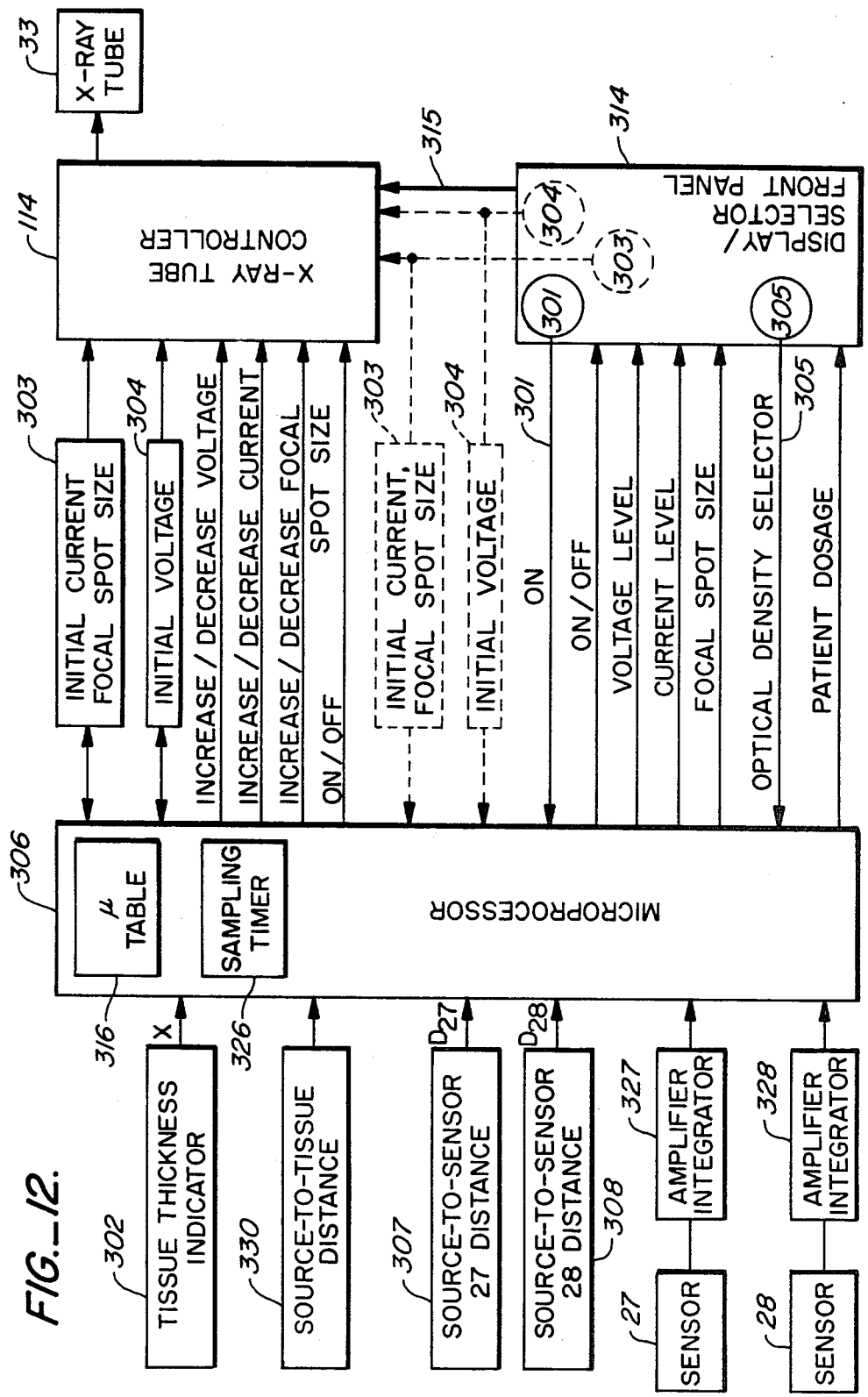

METHOD AND STRUCTURE FOR OPTIMIZING RADIOGRAPHIC QUALITY BY CONTROLLING X-RAY TUBE VOLTAGE, CURRENT, FOCAL SPOT SIZE AND EXPOSURE TIME

FIELD OF THE INVENTION

This invention relates to medical X-ray image radiographic quality and particularly to a method and structure for achieving optimum image quality by optimizing X-ray voltage, current, and exposure time for a given object to be radiographed.

BACKGROUND OF THE INVENTION

In medical diagnosis, an X-ray radiograph showing the image of tissues requires both sharp contrast and high resolution to show outlines of structures in the tissue which may be similar in composition to adjacent structures or may be physically small. The exposure of the X-ray film must also be carefully controlled to achieve optimum quality of the exposed film. Image quality in an X-ray film depends upon three factors: the contrast in film blackness between tissue structures of slightly different composition, the sharpness or resolution at edges of different structures, and the average density of exposed film particles. Thicker or denser tissue requires more radiation to achieve properly exposed X-ray film.

There is particular interest in use of X-ray filming for mammography. In most mammographic applications, the optimal exposure time for an X-ray film is 0.6–3.0 seconds. A longer time than 3 seconds might cause excess radiation to the patient, excess heating of the X-ray anode, and blurring of the film due to tissue motion during exposure. A shorter time than about 0.6 second might not offer the sharpest film contrast and highest resolution. Therefore other parameters of the X-ray equipment are selected in order to achieve a proper exposure within this time window. In particular the voltage and current applied to the X-ray anode are selected to optimize the image.

The voltage between cathode and anode of the X-ray tube is optimum when it produces X-ray photons of an energy range such that the particular tissue to be exposed absorbs a sizable number of X-ray photons in its more dense structures (those having higher atomic number) while passing more photons through its less dense structures. A lower peak voltage applied to the X-ray tube produces lower energy X-ray photons which are more easily absorbed by any tissue. For soft tissue the photon energy range must be fairly low to produce a clearly visible difference in the absorption rate of similar structures such as fat, blood vessels, and glandular tissue, none of which absorb photons as readily as bone, calcifications, or cartilage, for example. For a tissue which is fairly dense or fairly thick, the photon energy must be higher in order to avoid having too large a portion of the photons absorbed within the tissue. The goal is to permit an optimum percentage of the X-ray photons to pass through the tissue and into the film. In X-raying bones, the voltage which will distinguish between the bones having an average atomic number of about 13 and surrounding muscle (atomic number about 7.5), fat (atomic number about 6), and other soft tissue (average atomic number about 7.5) is not critical, as these adjacent tissues are quite different in composition. In mammography, however, where the X-ray film must distinguish between fatty tissue having an atomic number of about 6 and glandular tissue having an atomic number of about 7.5, a carefully selected peak voltage is needed in order to take advantage of the difference in absorption rate of these structures having similar composition.

For a given voltage and a given exposure time, the proper exposed film density can be obtained by controlling the X-ray flux (the number of X-ray photons per unit area per unit time). X-ray flux is proportional to current from cathode to anode in the X-ray tube. Maximum current in an X-ray tube depends on the power rating for the tube which in turn depends on the intended exposure time. As exposure time increases, maximum operating power (to avoid overheating the anode and other negative effects) decreases. For a given exposure time the power rating is constant, so that increasing the voltage results in a decrease in maximum current. Maximum current also depends on the area of the anode impinged by electrons and from which X-rays are emitted. The impinged area of the anode as projected in the direction X-rays are emitted is called the focal spot size. The power rating can be increased by increasing the size of the focal spot. However, a larger focal spot size decreases the sharpness of the film image, thus it is desirable to minimize focal spot size and therefore current in order to achieve maximum resolution of the film image. Another option for increasing sharpness when a larger focal spot size must be used and sharpness is also needed is to either locate the object to be radiographed close to the film or to move the source of the X-rays farther from the object. This effect is shown in FIGS. 1a and 1b. Objects 13-a and 13-b are located closer to the film in FIG. 1b than in FIG. 1a and thus show smaller blurred areas 16-a-b and 16-b-b than the blurred areas 16-a-a and 16-b-a shown in FIG. 1a.

Currently, an X-ray technician in preparing to X-ray a particular patient, estimates the density and thickness of the tissue to be penetrated by the X-ray beam and sets the voltage and current (or focal spot size) of the machine to achieve optimum contrast with optimum sharpness. A machine may be controlled manually by a technician who also estimates optimum exposure time and sets the machine for that time. When a more automatic machine turns on it will operate at the set voltage and current until a sensor indicates sufficient film darkening has occurred, at which time the sensor will automatically turn off the machine.

Such a prior art sensor will automatically achieve film darkening which is within an optimum range though film darkening can vary by as much as 30% even when an automatic sensor is used. This use of a sensor to control exposure time is well known and satisfactory for X-raying bones and other tissues in which there is sharp contrast between adjacent structures, however when X-raying soft tissue, the energy of X-ray photons, the flux of emitted photons, and the exposure time must all be accurately controlled in order to get good contrast between the similar structures within the soft tissue.

For a given operating voltage, the exposure time must be adjusted to achieve optimum film blackness. However, if the exposure duration is predicted to be too long, thereby introducing blurring of the film due to tissue motion during the filming, the operating voltage must be increased, thus sufficiently exposing the film in a shorter time. It is desirable to use the lowest possible photon energy and thus the lowest operating voltage in order to achieve the maximum contrast between tissue structures which are similar in their X-ray absorption and thus difficult to distinguish on an X-ray film. Another way to shorten the exposure time, achieving a sufficiently black film without increasing operating voltage, and thus reducing contrast, is to increase the operating current and thus increase the X-ray flux (the number of X-rays per second per unit area being delivered by the machine). Still another way is to use more sensitive film. An increased flux shortens the exposure time needed to achieve a given density of exposed film particles, since density of exposed film particles is directly proportional to the flux multiplied by time. An increased flux is achieved by increasing the size of the focal spot on the X-ray tube anode while also increasing the current of electrons hitting this focal spot. In some X-ray systems it is also possible to shorten the source to tissue distance in order to increase the X-ray flux passing through the tissue. This action has a number of limitations including higher surface exposure dose for the exposed tissue, degradation of resolution, less space to position the patient comfortably, and others.

It is not possible to increase the current to a focal spot of a given size beyond the rated current without melting that spot on the anode, thus to increase current the electrons must be defocused to impinge on a larger anode area, in turn causing X-rays to be emitted from a larger area. This larger area produces a reduction in sharpness of the film image as can be seen in FIGS. 1a and 1b (prior art). FIGS. 1a and 1b depict an X-ray source, collimator, objects to be shown on film, and the film. As shown in FIG. 1a, the size of the focal spot causes a defocusing of the image on the film, generating small penumbrae 16-a-a and 16-b-a. However, as shown in FIG. 1c, when the size of the focal spot is increased in order to increase the flux and decrease the exposure time, the size of this blurred area also increases.

FIGS. 2a, 2b, and 2c show film darkening along lines 2a, 2b, and 2c in FIGS. 1a, 1b, and 1c respectively. The penumbrae generally numbered 16 indicate areas of unsharpness in the image. It is desirable to keep these areas as small as possible. Note in FIG. 2a that the entire small object 13-b is represented by penumbrae 16-b-a and might well be unobserved on film. One way to reduce this blurring is to locate the object to be radiographed close to the film, as shown in FIGS. 1b and 2b, another is to move the X-ray source farther from the object. It is desirable to keep the focal spot size as small as possible to avoid defocusing from the larger focal spot in FIG. 1c.

In order to provide a quantitative understanding of the relationship between film optical density (darkness) and operating voltage, operating current, exposure time, tissue atomic number, tissue thickness and distance from X-ray source to film, the following mathematical explanation is provided.

The energy of photons emitted from the X-ray tube falls within an energy spectrum such as those shown in FIG. 3. The maximum photon energy emitted from an X-ray tube equals the maximum energy of the cathode stream electrons impinging on the X-ray tube anode, which in turn depends on the peak applied voltage between the cathode and anode of the X-ray tube and on the voltage wave form. Emitted photons have an energy spectrum which depends on the anode composition as well as the cathode-to-anode voltage drop. FIG. 3 shows energy distribution of emitted photons for tungsten and molybdenum targets when operated at voltages of 24 kilovolts and 28 kilovolts, respectively.

The X-ray flux, or number of emitted X-ray photons per second per unit area, varies as the square of the cathode-to-anode peak voltage and inversely as the square of the distance from the anode:

$$I = cV^2/D^2 \qquad (1)$$

where
I is X-ray photon flux,
V is X-ray tube peak operating voltage,
D is the distance from the anode to the point where flux is measured, and
c is a proportionality constant.

As the X-ray photons pass through an object which attenuates X-ray flux, they are attenuated according to the exponential attenuation law:

$$I_{out} = I_{in} e^{-\mu x} \qquad (2)$$

where
$I_{out}$ is flux of X-ray photons after passing through the object,
$I_{in}$ is flux of X-ray photons before passing through the object,
$\mu$ is the attenuation coefficient of the object at the particular X-ray energy, and
x is the thickness of the object.

Since attenuation coefficient $\mu$ is a function of photon energy, the energy distribution of X-rays after passing through an object differs from the incident energy distribution.

Attenuation of the emitted X-rays varies with atomic number of the material through which the X-rays pass as well as with the energy of the X-ray photons. X-ray flux is attenuated as it passes through an object for two reasons: absorption and scatter. Absorption attenuation is directly proportional to the third power of the average tissue atomic number and inversely proportional to the third power of photon energy, which is directly proportional to voltage. Thus, $$\mu_{abs} = g \frac{Z^3}{V^3} \qquad (3)$$

where
$\mu_{abs}$ is the attenuation coefficient due to absorption,
Z is the atomic number of the tissue, and
V is the operating voltage of the X-ray machine.
g is a proportionality constant.

Scatter attenuation (the Compton effect) decreases inversely as operating voltage increases and is largely independent of tissue atomic number.

$$\mu_{sc} = f \frac{1}{V} \qquad (4)$$

where
$\mu_{sc}$ is attenuation coefficient due to scatter, and
f is a proportionality constant.
Thus, the total attenuation coefficient on passing through an object due to both absorption and scatter is $$\mu = g\frac{Z^3}{V^3} + f\frac{1}{V} \qquad (5)$$

Thus, X-ray flux after passing through an object is $$I_{out} = I_{in}e^{-(gZ^3/V^4 + f/v)x} \qquad (6)$$

Darkening rate of the X-ray film is directly proportional to X-ray flux at the particular location on the film. Thus it is clear why the operating voltage of the X-ray tube is important in controlling the contrast of the film, and why contrast between structures of slightly different average atomic number increases as operating voltage decreases.

In the past, it has been known that optimum operating voltage is a function of tissue absorption coefficient or tissue density. X-ray technicians have generally used tables of optimum operating voltage and current as a function of tissue density.

For X-raying dense tissue such as bone ($Z \approx 13$) the preferred X-ray tube voltage is around 85 kilovolts. For soft tissue ($Z \approx 7$) the preferred voltage for achieving moderate attenuation within the tissue is 20 to 35 kilovolts. When using a molybdenum target X-ray tube for a mammogram, for an average size breast having an average proportion of glandular tissue and thus an average atomic number of approximately 6.8, an average density of about 0.98, and an average compressed tissue thickness of 4–5 cm, a 28 kilovolt setting gives optimum contrast. For an average size breast having a high proportion of fatty tissue with an average atomic number of 6, a density of approximately 0.9, and an average compressed tissue thickness of 4–5 cm, a 26 kilovolt setting gives optimum contrast. For an average size breast dense in glandular tissue and having an average atomic number of approximately 7.5, a density of about 1.05, and compressed tissue thickness of 4–5 cm, a 30 kilovolt setting gives optimum contrast. For a large breast dense in glandular tissue having a compressed tissue thickness of 6–7 cm, a 32 kilovolt setting gives optimum contrast. When using a tungsten target X-ray tube, voltage settings for an average size breast having fatty, average, dense glandular, and thick dense glandular composition will be 23, 24, 25, and 26 kilovolts, respectively. A lower voltage setting gives higher film contrast but requires longer exposure time and results in more radiation absorption to the tissue.

As can be understood from the thickness factor x in equations 2 and 6, thinner tissue requires less radiation for proper film exposure. Thinner tissue also produces a film where structures are easier to observe because fewer structures are superimposed one above another. In the case of a mammogram, the breast is compressed between parallel plates in order to reduce the thickness which must be penetrated by the X-ray beam. Compression can result in a reduction of X-ray tube operating voltage from 30 to 35 kilovolts for an uncompressed breast to 22 to 24 kilovolts (tungsten X-ray tube) for the breast when compressed. This voltage reduction increases film contrast without producing increased radiation exposure to the patient. Such compression has the additional advantage of providing tissue of uniform thickness over most of the area being radiographed and thus improving quality of the produced film. In addition improved quality occurs because fewer tissue structures are superimposed, and there is less scatter radiation. Therefore breast compression is a widely used technique today.

If the technician has not properly estimated average tissue density, the selected voltage and current may not produce optimum contrast and sharpness. After developing the film, the technician or the radiologist may discover that it is necessary to take another film, using a different voltage or current in order to achieve a good enough quality film for a reliable diagnosis.

A method and device are desired which give good film quality in every film in order to reduce the radiation dosage to the patient, the cost of producing a satisfactory film, the inconvenience and discomfort to the patient, the need for technician expertise and experience, and the need for a radiologist to be present to examine the film, thus giving a high patient throughput and lower fees. In particular, in the field of mammography, there is need for a better method and device to produce mammograms quickly and accurately so that a radiologist can make an accurate diagnosis, while the patient receives the service at low cost and doesn't have to wait to see if the X-ray image was satisfactory or return for another session.

SUMMARY

Whereas in the prior art, sensors such as ionization detectors have been used to control only the duration of an X-ray exposure to automatically achieve proper density of blackened particles in the X-ray film, the structure and method of this invention also adjust the operating voltage and current of the X-ray machine and focal spot size of the X-ray source to account for the particular characteristics of the tissue being examined, thereby achieving an optimum image in every film.

The method and structure of this invention sample the transmitted signal over a short period of time at the beginning of an X-ray exposure and adjust both the peak voltage and the focal spot size (and current) in the X-ray tube, thereby accurately controlling the photon energy and the flux of the X-rays generated by the tube in addition to controlling the exposure time as in prior art devices and methods. This careful selection of voltage, current, focal spot size and time gives the radiologist the highest radiographic contrast and sharpness on the X-ray film, which in turn gives the best diagnostic image. In mammography, an increased diagnostic accuracy permitting a definitive and correct radiographic interpretation results from an improved visualization achieved with the present invention. This permits a substantial reduction in the number of biopsies ordered because of uncertainty and which in fact show benign breast lesions. The increased accuracy will increase the early diagnosis of breast malignancies. The teaching of this invention provides improved quality X-ray film when examining other soft tissues as well, and of course this invention is not limited to use with soft tissues or even to medical applications.

With this invention the technician needs less experience and expertise to operate the machine properly, the patient is subjected to less discomfort, inconvenience, and radiation exposure. The radiologist does not have to be present to examine the exposed film for quality at the time of production, there is no wasted film, and the patient does not have to return for retakes. Additionally, the throughput for one X-ray machine is increased with a resulting decrease in the cost of serving the patient.

According to the method of this invention, a technician may initially set voltage and focal spot size according to experience and observation of the particular tissue to be radiographed, or the machine may be designed to begin all exposures at a typical setting. Of importance, a sampling period then occurs at the beginning of every exposure. A sensor located beneath the tissue being exposed detects the level of received radiation. Some means is used for determining the thickness of the tissue being exposed, for example manual measurement followed by entering the value into a microprocessor or in the case of mammography with breast compression, automatically determining the thickness of the compressed breast from the compression device and supplying this value to a microprocessor. From the initial voltage and current settings, the tissue thickness, and the radiation detected by the sensor, a microprocessor calculates the attenuation of X-ray flux caused by passing through the tissue and determines the average density of the tissue and the expected total exposure time. This calculation occurs during a small portion of the shortest possible exposure time. For conventional X-ray machine technique using high voltage and total exposure time of 50 to 100 milliseconds (a typical exposure time for a chest X-ray), the sampling time might be 5 milliseconds. In mammography, where the exposure time is on the order of a few seconds, the sampling time may be 100 to 200 milliseconds. In X-raying the pelvis or the extremities where total exposure time is 5 to 10 seconds, the sampling time may be up to 1 second, though a shorter sampling time is usually sufficient. A short sampling time such as 5 milliseconds is sufficient for providing the information to adjust exposure, however the sensor and other electronic components needed to detect radiation during a short sampling time are more expensive, thus a longer sampling time may be chosen when total exposure will be longer, in order to save cost of the components.

If the density calculation indicates contrast will not be optimum, the microprocessor causes the X-ray tube voltage to be adjusted to its optimum value. If the calculated exposure time is outside the accepted range, the microprocessor also causes the X-ray tube current and focal spot size to be adjusted. Then for the remainder of the exposure time the X-ray photon energy and X-ray flux are optimum for the particular tissue. Rather than optimizing only the exposure time as was done in the prior art, the method and structure of this invention optimize voltage, current, and focal spot size as well, thereby achieving not only optimum film darkness but also optimum contrast and optimum resolution.

Although the above description relates to medical applications and particularly to mammography, the principle of the invention, namely sampling the received signal during the early part of the exposure and adjusting voltage, current and focal spot size, also applies to industrial uses. For example, when X-rays are used in the inspection of printed circuit boards and the thickness of deposited metal varies, an ideal film or other recording will be achieved when voltage and possibly current are adjusted after a short sampling period to compensate for the variation in thickness. For another example, when an X-ray method and machine are used to inspect a pipeline for cracks or other sharp defects, periodically sampling X-ray radiation as the pipeline moves before the X-ray machine and adjusting voltage and current to compensate for a varying pipeline thickness achieves an optimum recording of all information as thickness varies.

BRIEF DESCRIPTION OF THE DRAWINGS

FIGS. 1a, 1b, and 1c show the relationship between distance from object to film and blurring caused by the size of a focal spot from which X-rays are generated;

FIGS. 2a, 2b, and 2c show film darkening of film shaded by objects shown in FIGS. 1a, 1b, and 1c respectively along respective cross sectional lines.

FIG. 3 shows X-ray spectra for tungsten and molybdenum X-ray tubes used with this invention;

FIGS. 4, 5, and 6 show the relationship between X-ray source, positioning apparatus, compressed breast, and sensors used in three embodiment of this invention for mammography;

FIG. 7 is a graph showing the Heel effect;

FIG. 8 shows the relationship between exposure time and film darkness for voltage ranges which are too high, too low, and correct for optimum film contrast;

FIG. 9 shows a prior art device for automatically controlling exposure time;

FIG. 10 shows the relationship between film optical density (blackness) and exposure;

FIG. 11 shows an embodiment of this invention for controlling voltage, current and focal spot size; and FIG. 12 shows an embodiment of this invention for controlling voltage, current, focal spot size and exposure time and for displaying these parameters.

DETAILED DESCRIPTION

FIGS. 4, 5, and 6 show three embodiments of the components used with this invention. The components of FIGS. 4, 5, and 6 are shown for mammography, though of course the invention is not limited to use with mammography.

In all three figures, X-ray source 11 emits radiation having characteristics determined by the X-ray tube voltage, current, and focal spot size. This emitted radiation leaves the X-ray source at a wide angle of radiation. Collimator 12 absorbs radiation not within the X-ray opening angle a. Soft radiation filter 13, typically of molybdenum, aluminum, cadmium or copper is located between source 11 and collimator 12, often adjacent to source 11. It absorbs most of the soft radiation. As shown in FIG. 7, radiation is present over the entire collimator opening 12 but because of the Heel effect, in which some of the radiation emitted by the X-ray tube anode 11 is actually absorbed within the anode itself, the intensity of emitted radiation decreases as the direction of emission becomes less perpendicular to the anode surface. The radiation then passes through breast compression plate 21, which may be made of flexible polycarbonate, fiber carbon, or another material which transmits X-rays. It then passes through the compressed breast 22 having compressed thickness $x_{22}$.

Shown in FIG. 4 is grid device 23 of thickness $x_{23}$ which is usually of lead, having vertical columns through which X-rays can pass. Such a grid device absorbs scatter radiation moving at an oblique angle, and significantly improves the film contrast, especially for tissues which scatter a significant amount of the radiation incident on the tissue. The grid also absorbs some of the direct radiation transmitted through the tissue, therefore the exposure time will be longer. In mammography exposure time is longer by a factor of about 2.5–3.0 when a grid device is used.

Beneath grid device 23 is film/screen cassette 24. The cassette is made of an X-ray transparent material, hard or soft (for example a black nylon bag), to avoid further absorption of radiation by the cassette and therefore minimize the dose to the patient. The cassette encases a film to be exposed and provides protection to the film from light and mechanical damage. A layer of film having crystals of a chemical sensitive to X-ray radiation is located within the cassette. The radiographic contrast depends upon the particular film being used, and exposure time provided by the microprocessor must be matched to the film being used. In order to increase sensitivity some cassettes have adjacent to the layer of film a film screen which is sensitive to X-rays. Upon receiving a single X-ray photon, the film screen emits about 30 to 40 photons which in turn expose the film, thus magnifying the effect of a single X-ray photon. These emitted photons are of a different frequency from the X-rays, therefore a different film must be selected to be responsive to the wavelength of these emitted photons.

Breast tray table or top cover 25 is shown in FIG. 4 as located beneath grid 23 and film cassette 24. The tray is also made of a material which does not absorb X-rays. It serves a structural purpose. In FIG. 5 this tray 25 is shown located above the grid and film cassette.

In both FIGS. 4 and 5, sensors 27 and 28 detect the rate of received radiation. Sensor 27 detects radiation transmitted through the tissue to be examined, and sensor 28 serves to provide a calibration level which is used by the microprocessor for comparison. The sensors may be ionization chambers, scintillators, semiconductors, or other suitable detection devices. Semiconductor sensors may be silicon or germanium photodiodes. Current generated by these sensors is related to the type and size of the sensors, the number of X-ray photons impinging on them, and only weakly to the energy of the impinging X-ray photons. Current generated by sensor 27, located beneath film screen cassette 24 is approximately proportional to the rate of darkening of the film in the cassette.

The microprocessor uses this sensor information to calculate estimated exposure time, optimum X-ray tube voltage, focal spot size, and current, and sends signals to the X-ray equipment which set voltage, current and focal spot size to their optimum values, as will be explained.

In order to assure that total exposure time falls within the acceptable maximum (not producing blurring from tissue motion during exposure, over-exposing the patient, or overheating the X-ray anode) the current to the X-ray tube and the resulting flux of generated X-ray photons must be sufficient to generate the required radiation within the required time. An increased current will proportionally increase the radiation rate (the flux) and thus decrease the time required for the exposure. However, the spot on the X-ray tube anode on which the electrons impinge must not be heated to the melting point. Therefore if the current must be increased, the size of the focal spot on which the electrons impinge must be increased. Rather than offering a continuum of focal spot sizes, most X-ray tubes of today offer a choice of two or three focal spot sizes. If the exposure time using the smallest focal spot size will be exceeded, the tube must be switched to a larger focal spot size, and to a corresponding higher current, resulting in a shorter total exposure time.

FIG. 8 shows the relationship between exposure time and film darkness for five voltage ranges. Curve 1 achieves sufficient film exposure in less than one second. This occurs when photons penetrate the tissue very easily and are absorbed only slightly by the tissue. Thus, at a voltage with a high tissue penetrability the film ionization rate is higher, the slope of the curve in FIG. 8 is higher, and the total exposure time is shorter. A radiographic film of soft tissue taken at such a voltage will show little contrast between adjacent soft tissue structures, none of which attenuate a significant proportion of the incident photons. Curve 5 requires about 4 seconds to achieve sufficient film exposure. In this case a large proportion of the incident photons are absorbed by the tissue. There will be high contrast between differing soft tissue structures, because slight differences in density and atomic number produce significant differences in attenuation. However there is likely to be degradation of picture quality due to tissue motion during a long exposure and the increased X-ray absorption within the tissue produces a high radiation exposure to the patient. Curve 3 shows the relation between exposure time and film darkness for operating voltage producing X-ray photons having the correct penetrability of the particular tissue. In this case, the exposure time is within the preferred range, contrast between soft tissues of similar composition is sufficient, radiation dosage to the patient is minimized, and tissue motion is not likely to cause blurring.

According to one embodiment of this invention, if sensor measurements taken during the short sampling time $t_s$ shown in FIG. 8 give an integrator voltage at the end of the sampling time between points 92 and 94, indicating that the initial operating voltage is producing photons having a tissue penetrability within 25% of the optimum level, no change is made in either the operating voltage or the focal spot size and current. If sensor measurements produce an integrator voltage between points 91 and 92, indicating tissue penetrability is between curves 1 and 2 of FIG. 8, the voltage is decreased to bring tissue penetrability within the optimum range between curves 2 and 4. If the integrator voltage is between points 94 and 95 indicating tissue penetrability is between curves 4 and 5, tube operating voltage is increased to bring penetrability within the desired range.

If the integrator voltage is above point 91 indicating tissue penetrability is so high that the integrator voltage representing film darkness will be reached in less than 1 second both operating voltage and focal spot size are decreased to achieve optimum resolution and contrast. Of course if focal spot size is already at its minimum size, some machines can be set to decrease current independently and some will simply be controlled to use the very short exposure time. This situation can occur with very thin tissues, and will not produce degradation in film quality.

If the integrator voltage at the end of the sampling time is below point 95 in FIG. 8, indicating total exposure time will exceed the maximum exposure time allowed by the tube rating or by expected blurring due to tissue motion, both operating voltage and focal spot size are increased in order to bring the total exposure time within the desired range.

In order to accurately determine the density of the tissue to be exposed, the presence of grid device 23, film/screen cassette 24, breast tray 25, and any other absorbing devices between source and sensor must be accounted for. Each of these has an absorption coefficient $\mu$ and a thickness x. The equation for radiation reaching sensor 27 after passing through absorbing objects 22, 23, 24 and 25 is $$I_{27} = I_{27a} e^{-(\mu_{22} x_{22} + \mu_{23} x_{23} + \mu_{24} x_{24} + \mu_{25} x_{25})} \quad (7)$$

where $I_{27}$ is radiation flux reaching sensor 27, $I_{27a}$ is radiation flux at sensor 27 when absorbing objects 22, 23, 24 and 25 are not present $\mu$ is absorption coefficient indicating flux remaining after transmission through the subscripted layer, x is the thickness of the subscripted layer, and subscripts correspond to the numbers in FIGS. 4 and 5.

FIGS. 4 and 5 show sensors 27 and 28 located below the film cassette 24 and sensor 29 located above all absorbing layers. Sensor 29, shown in dotted lines, is in an alternative location for the calibration sensor 28 which receives radiation not passed through tissue. Sensors 27, and 28 or 29 must be calibrated in order to account for (1) the distance from the source to each of the sensors, (2) the nontissue materials in the path from source to sensor, (3) the size and efficiency of the sensors, and (4) the Heel effect (see FIG. 7), which is a decrease in X-ray flux emitted from the source as the angle at which X-rays leaving the anode becomes less perpendicular to the anode surface. By measuring sensor current to each sensor at a known X-ray tube current and voltage with no tissue present, normalization factors can be determined which account for all these effects. The sensor current which flows with no tissue present will differ from current with tissue present by the absorption coefficient of the tissue multiplied by tissue thickness.

$$i_{27} = i_{27-0} e^{-\mu x} \quad (8)$$

where $i_{27}$ is the current through sensor 27 with tissue present $i_{27-0}$ is the current through sensor 27 with no tissue present $\mu$ is the absorption coefficient of the tissue x is the thickness of the tissue A normalization factor also exists between calibration sensor 28 and exposure sensor 27. This can be determined by measuring current through the two sensors with no tissue present and taking the ratio.

$$N_{27-28} = i_{27}/i_{28} \quad (9)$$

where $N_{27-28}$ is the normalization factor for sensor 27 when used with sensor 28, $i_{27}$ is the current through sensor 27, and $i_{28}$ is the current through sensor 28.

Since radiation reaching sensor 28 is $$I_{28} = I_{28a} e^{-(\mu_{23} x_{23} + \mu_{24} x_{24} + \mu_{25} x_{25})} \quad (10)$$

where $I_{28}$ is radiation reaching sensor 28 and $I_{28a}$ is radiation which would reach sensor 28 if absorbing layers 23, 24, and 25 were not present and since sensor current is proportional to radiation flux reaching the sensor, the ratio of current from sensors 27 and 28 during tissue exposure, assuming the distance from the source to the two sensors is unchanged after calibration is $$i_{27}/i_{28} = N_{27-28} e^{-\mu_{22} x_{22}} \quad (11)$$

Thus, the absorption coefficient for the tissue is $$\mu_{22} = \frac{\ln N_{27-28} + \ln i_{28} - \ln i_{27}}{x_{22}}. \quad (12)$$

The second sensor may be located anywhere in the path of the beam, for example in the place where sensor 29 is located. In this case, a different normalization factor is used to calibrate sensors 27 and 29 during the installation of the device. In this case, $$\mu_{22} = \frac{\ln N_{27-29} + \ln i_{29} - \ln i_{27}}{x_{22}}. \quad (13)$$

Therefore using two sensors, one of which detects radiation passing through the tissue and through other structures, and one of which detects radiation passing through other structures but not passing through the tissue, allows a microprocessor to make an accurate calculation of tissue density regardless of the thickness or presence of absorbing layers such as 23, 24, and 25.

Equations 9, 11, 12, and 13 above assume distance from source to sensor is constant after calibration. If the X-ray apparatus is to provide the option of varying the distance from source to sensor (to film) and the distance from the source to the two sensors is not equal, the normalization factor must not ignore the distances as in equation 9. Instead a different normalization factor is calculated $$i_{27}/i_{28} = N'(D_{28}^2/D_{27}^2) \quad (14)$$

or $$N' = (i_{27} D_{27}^2 / i_{28} D_{28}^2) \quad (15)$$

Where $N'$ is a normalization factor for sensor 27 and 28, $D_{27}$ is distance from source 11 to sensor 27, and $D_{28}$ is distance from source 11 to sensor 28.

In this case the absorption coefficient for tissue being exposed is $$\mu_{22} = \frac{(\ln N' + 2 \ln D_{28} + \ln i_{28} - 2 \ln D_{27} - \ln i_{27})}{x_{22}} \quad (16)$$

When a single sensor 26 is used, the four factors affecting sensor calibration, namely distance, intervening nontissue material, sensor size and Heel effect factor, are all the same; therefore, if distance from source to sensor is constant the normalization factor $N_{26-26}$ is 1, and $$\mu_{22} = \frac{\ln i_{cal} - \ln i_{exp}}{x_{22}} \quad (17)$$

where $\mu_{22}$ is absorption coefficient for tissue 22, $i_{cal}$ is sensor current during calibration, $i_{exp}$ is sensor current during exposure, and $x_{22}$ is the thickness of tissue 22.

In the embodiment of FIG. 6, the single sensor 26 is used for calibration before the patient is positioned for exposure and then used again during exposure. The reading from single sensor 26 taken during exposure is used by a microprocessor just as the reading from sensor 27 taken during exposure would be used. Calibration information from sensor 26 taken before and during exposure is fed to the microprocessor. Also fed to the microprocessor is an indication of tissue thickness. This tissue thickness information may be entered manually by a technician or preferably may be taken from the position of the tissue compression device. With a single sensor, if the device will be used at variable distances during operation, the distance factor must be included in the calculation of tissue absorption coefficient, in which case $$\mu_{22} = \frac{(\ln i_{cal} + 2 \ln D_{cal} - \ln i_{exp} - 2 \ln D_{exp})}{x_{22}} \quad (18)$$

A single sensor device has the advantages of being less expensive to manufacture and more compact mechanically and therefore easier to manipulate. However, it requires more frequent calibration to give accurate results. The single sensor machine of FIG. 6 is used just as the machine of FIG. 4 is used, with the microprocessor making a calculation of optimum voltage and current during a sampling period up to the first approximately 200 milliseconds of tissue exposure.

Two embodiments of logic used to achieve optimum control are now described, one shown in FIG. 11 which is simple and low in cost, and one shown in FIG. 12 which provides maximum flexibility with minimum need for technician expertise. First, however, in order to provide understanding of the voltage and focal spot size control of this invention, the automatic timing control used with this invention and shown in FIG. 9 will be described. It will then be shown that with the method and structure of this invention the control of exposure time to achieve optimum film darkness can also be improved.

When a sensor is exposed to radiation it begins to conduct current which is proportional to the amount of radiation per unit time reaching the sensor, and only weakly related to X-ray photon energy or operating voltage.

$$i = k \, E/t \quad (19)$$

where
  i is sensor current
  k is a proportionality constant
  E is radiation dosage or exposure
  t is time.

As shown in FIG. 9, the output of sensor 27, having a value on the order of nanoamperes, is fed to preamplifier 101, which provides an output having a voltage on the order of millivolts. The output of preamplifier 101 is fed to noise filter 102, which may consist of a large capacitor in parallel with a large resistor. This filter removes any noise spikes, and any current which leaks from the sensor with no ionization present, which might negatively affect integrator 103 which receives the signal from filter 102. Integrator 103 may comprise capacitor 104 in parallel with relay controlled switch 105. When relay switch 105 is opened, integrator 103 begins to integrate the input signal from filter 102 by charging capacitor 104. Capacitor 104 continues to charge until relay controlled switch 105 is closed, at which time capacitor 104 is discharged through switch 105, and the process may begin again for a new exposure. Calibrator 107 provides an amplification voltage related to sensitivity of the film or film screen being used. For a sensitive film or film screen, calibrator 107 causes a high amplification so that the output signal from amplifier 106 will rise more quickly. This output signal is fed to fine tuner 108 which in turn provides an output signal higher or lower or the same as its input voltage depending on an input signal from optical density selector 109.

An optical density of 1.0 indicates a film blackness in the middle of the linear range of film exposure. FIG. 10 shows a characteristic curve of film optical density as a function of the logarithm of film exposure (flux times exposure time). The curve is steepest around an optical density of 1.0 which means that if the average optical density over the surface of the film is 1.0 there will be maximum contrast between structures giving less film exposure and other structures giving more film exposure.

Optical density selector 109 allows for manual adjustment of film optical density. In one embodiment of this invention, selector 109 provides a 20% variation in optical density between one step and the next and provides nine steps with labels from $-4$ to $+4$ where the step labeled "0" provides no adjustment in optical density. If the radiologist will need a dark film of 1.6 optical density units, then he sets the optical density selector to step $+3$ and if he needs light film of 0.6 optical density units then he selects step $-2$.

Optical density selector 109 serves a second function. If the radiologist or technician is using a film for which the calibrator 107 is not intended, the mismatch may be compensated for by adjusting density selector 109. For example if an optical density setting of 0 gives an optical density of 1.0 in a film screen cassette with a typical sensitivity, then a density selector setting of $-2$ will give an optical density of 1.0 using a 40% more sensitive film screen cassette combination than the machine is calibrated for.

Comparator 111 compares the output signal from fine tuner 108 to a reference voltage from reference voltage generator 110. When the voltage from fine tuner 108 rises past reference voltage 110, comparator 111 cause SCR-relay 112 to send a turn-off signal to adaptor/interface 113 which causes X-ray controller 114 to turn off X-ray tube 33. SCR-relay also closes switch 105 causing integrator 103 to reset capacitor 104.

An automatic exposure control such as that in FIG. 9 which produces a controlled amount of radiation to sensor 27 will produce some variation in darkness of film being exposed when X-ray photons of a constant peak energy are passed through tissue of varying density or thickness. Table 1 shows empirical measurements of optical density of exposed film when exposing compressed breast tissue of varying thickness for constant X-ray tube operating voltage. The exposure time as determined by using a sensor with components shown in FIG. 9 varies from 0.9 sec to 3.2 sec. Rather than exposing the film to an optimum optical density near 1.0, the automatic sensor actually produces a 30% range in film optical density from 0.9 to 1.2.

This is because sensor 27 receives a different energy spectrum than the film being exposed. The film, which is between the sensor and the source, absorbs soft radiation in a higher proportion than it absorbs total radiation, so that for thin tissue in which much soft radiation reaches the film and is absorbed by it, there will be a smaller proportion of soft radiation passing to the sensor and thus a smaller ratio of sensor flux to film flux. Therefore a constant total sensor radiation produces an overexposed film for thin tissue.

By contrast, the method of this invention, which has been tested using a phantom model for breast tissue known to give results reliably close to measurements for humans, has produced the nearly constant optical density results shown in Table 2. Reducing operating voltage when X-raying thin tissue results in more absorption of soft radiation by the tissue, so that the ratio of film flux to sensor flux remains nearly constant.

TABLE 1
(Prior Art)

| Operating voltage (keV) | Thickness of compressed breast (cm) | Exposure Time (sec) | Optical Density of Exposed Film |
|---|---|---|---|
| 23 | 2 | 0.9 | 1.2 |
| 23 | 3 | 1.4 | 1.1 |
| 23 | 4 | 2.1 | 1.0 |
| 23 | 5 | 3.2 | 0.9 |

TABLE 2

| Operating voltage (keV) | Thickness of compressed breast (cm) | Exposure Time (sec) | Optical Density of Exposed Film |
|---|---|---|---|
| 22 | 2 | 1.6 | 1.1 |
| 23 | 3 | 1.4 | 1.1 |
| 24 | 4 | 1.4 | 1.0 |
| 25 | 5 | 1.2 | 1.1 |

As shown in FIG. 11, according to the method and structure of this invention, a simple method and device for controlling voltage and focal spot size without need for a microprocessor uses many of the same steps and same components as the method and device for controlling exposure time just described in conjunction with FIG. 9. The embodiment of FIG. 11 uses a single sensor 26 as shown in FIG. 6 and thus the machine with which it is used is more compact than a machine which must provide space for a second sensor. Components of FIG. 9 having identical function to those in FIG. 10 are given identical reference numbers. The signal from sensor 26 is sent through preamplifier 101 and noise filter 102 to integrator 103. As in the time controller of FIG. 9, integrator 103 of FIG. 11 may comprise a capacitor in parallel with a switch. However, rather than using voltage accumulated across the capacitor to control the turning off of the device and the turning off of integrator 103, the voltage and focal spot size controller of FIG. 11 uses sampling time indicator 204 to cause integrator 103 to provide a signal at the end of the sampling time to amplifier 106 which is calibrated by calibrator 107.

Fine tuner 108 and density selector 109 are equivalent to those in FIG. 9 already described. Comparator 211 differs from comparator 111 of FIG. 9 in that it compares the incoming signal to four voltage levels rather than one. Reference voltage levels equal to those of FIG. 8 labeled 91, 92, 94, and 95 are labeled V291, V292, V294, and V295 respectively and allow comparator 211 to discriminate between the five regions in FIG. 8 for which different kinds of adjustment in the voltage and focal spot size settings are made. If the incoming signal VA from fine tuner 108 is between reference voltage levels V292 and V294, the outgoing signal from comparator 211 causes X-ray controller 114 to make no change in the initial settings of X-ray tube 33. If incoming signal VA is less than reference voltage level V294, adaptor/interface 213 causes X-ray controller 114 to increase the operating voltage of X-ray tube 33 by a selected amount, equal to one kilovolt in an embodiment using a tungsten tube. If incoming signal VA is above reference voltage V292, adaptor/interface 213 causes X-ray controller 114 to decrease the operating voltage of X-ray tube 33 by a selected amount, also one kilovolt in this embodiment. If incoming signal VA is below reference voltage V295, adaptor/interface 213 causes X-ray controller 14 to increase the operating voltage of X-ray tube 33 by a selected amount, possibly more than one kilovolt in this embodiment and also to increase the focal spot size from its initial setting of typically 0.1 mm to 0.3 mm in diameter for mammographic diagnostic imaging or from an initial setting of 0.3 to 0.6 mm in diameter for mammographic screening while simultaneously increasing the tube current from its initial setting of typically 20 milliamperes to 50 milliamperes for diagnostic imaging or from 50 milliamperes to 100 milliamperes for mammographic screening. If incoming signal VA is above reference voltage V291, adaptor/interface 213 causes X-ray controller 114 to decrease the operating voltage of X-ray tube 33 by a selected amount, possibly more than one kilovolt in this embodiment and also to decrease the focal spot size from its initial setting while simultaneously decreasing the tube current from its initial setting. If different initial values of voltage, current and focal spot size have been set, the signals from the adaptor/interface will of course produce different final settings.

In the embodiment of FIG. 11, the voltage level of calibrator 107 is established by an experienced maintenance person at the time of machine installation and adjusted periodically thereafter.

FIG. 12 shows a preferred embodiment of the structure of this invention having fully automatic features, and having more flexibility than the embodiment of FIG. 11 and less need for frequent calibration. This embodiment allows for variable source to sensor distance and source to tissue distance. Additionally this embodiment provides for a front panel display which tells the technician the initial and final voltage and current settings, the tissue thickness and the source to film distance. This embodiment can also provide the technician or radiologist with a record of several absorbed dosages, for example maximum surface dosage, midpoint dosage, and average dosage of glandular tissue received by the patient. The components shown in FIG. 12 include two sensors however an embodiment similar to FIG. 12 can be provided having either a single sensor or multiple sensors.

The embodiment of FIG. 12 uses two sensors 27 and 28 as shown in FIG. 5. The signals from sensors 27 and 28 are fed into units 327 and 328 respectively which serve the functions of pre-amplifier 101, noise filter 102 and integrator 103 of FIGS. 9 and 11. Provided to microprocessor 306 are integrated output signals from units 327 and 328. These signals begin with a voltage level of zero at the time the machine begins to operate and steadily increase during the exposure period. Tissue thickness indicator 302, which may comprise a variable resistor in which resistance is proportional to tissue thickness provides input x to microprocessor 306.

Also provided to microprocessor 306 are distance indications from indicator 307 which indicate distance from source 11 (FIG. 5) to sensor 27 (assumed equal to or proportional to source to film distance) and indicator 308, which indicate distance from source 11 to sensor 28. Also provided are initial X-ray tube operating voltage setting and initial focal spot size from indicators 303 and 304, and optical density from manual optical density selector 305. The embodiment of FIG. 12 shows that initial current and focal spot size and initial voltage are selected by the microprocessor as the optimum current, focal spot size and voltage of the previous exposure. This embodiment is preferred for successive exposures to the same patient. A variation on this embodiment would have initial values established by the microprocessor automatically in response to manual entry of estimated tissue density by the technician. Another variation would have initial current, focal spot size and voltage established manually by a technician who is preparing the patient for exposure. In such an embodiment dials on front panel 314 would be used for providing initial voltage, current, and focal spot size indications to both microprocessor 306 and to X-ray tube controller 114. This alternative embodiment is shown in dotted lines.

Stored within microprocessor 306 is $\mu$-table 316 which gives tissue attenuation factor $\mu$ as a function of the ratio of voltage presented to microprocessor 306 by integrators 327 and 328 at the end of the sampling time, tissue thickness presented by thickness indicator 302, source to sensor 27 distance presented by indicator 307, source to sensor 28 distance presented by indicator 308, initial X-ray tube operating voltage indicated by indicator 303 and initial current indicated by indicator 304.

As an alternative, $\mu$-table 316 can give tissue attenuation factor as a function of the ratio of voltages presented by integrators 327 and 328 at the end of the sampling time, assuming that sensor distances are constant. Rather than calculating optimum voltage and current, the microprocessor calculates change in voltage and current needed to reach optimum values.

The values in $\mu$-table 316 depend on the type of anode being used, the thickness and composition of the soft radiation filter and other absorbing layers between the source anode and the sensor (26 or 27). Absorption of these non-tissue absorbing layers is a function of the X-ray photon energy. Generally the X-ray beam leaving the collimator 12 after passing through soft radiation filter 13 has a spectrum such as one of those shown in FIG. 3. The spectrum as well as the intensity will change as it passes through subsequent layers. The X-ray spectrum at the exit of the collimator will also change as tube voltage and voltage wave form change. For a particular system the nontissue absorbing layers will generally remain constant from one exposure to the next, while the tube voltage will generally change from one exposure to the next. Therefore a $\mu$-table can be developed for a particular machine which takes these absorbing layers into account and simply provides $\mu$ as a function of operating voltage.

The $\mu$-table for the particular machine may be determined by operating the machine with no tissue present at each voltage which will be used during an actual exposure, obtaining sensor current at each of these voltages and using equation 17 to determine the tissue absorption coefficient during an actual exposure.

Alternatively, if the spectrum of X-ray energy entering the tissue is known, this spectrum can be used to calculate tissue absorption coefficient. The spectrum may for example be similar to one of those shown in FIG. 3. The absorption coefficients of three kinds of breast tissue at a particular photon energy are shown in Table 3. These absorption coefficients are given by way of example. Absorption coefficients of other kinds of tissue and also of other industrial materials would be used as appropriate in determining a $\mu$-table for a particular X-ray machine and a particular use. The integral of the X-ray photon energy spectrum times the absorption coefficient at each energy gives an overall absorption coefficient of the tissue for the energy spectrum passing through the tissue.

Table 3 also illustrates the strong effect of tube voltage on tissue absorption and shows the importance of carefully controlling tube voltage during exposure.

TABLE 3

| | Tissue Absorption Per Centimeter Thickness for three kinds of breast tissue | | |
|---|---|---|---|
| Photon Energy | Fatty | Half Fatty/ Half Glandular | Glandular |
| 10 keV | 2.77 | 3.80 | 5.20 |
| 15 keV | 0.92 | 1.23 | 1.60 |
| 20 keV | 0.50 | 0.62 | 0.77 |
| 24 keV | 0.41 | 0.50 | 0.61 |
| 28 keV | 0.32 | 0.38 | 0.45 |
| 30 keV | 0.27 | 0.32 | 0.37 |
| 34 keV | 0.25 | 0.29 | 0.33 |
| 40 keV | 0.21 | 0.24 | 0.27 |
| 50 keV | 0.19 | 0.21 | 0.23 |

When a turn-on signal is provided to microprocessor 306 by a technician pressing button 301 on front panel 314, a timer 326 in microprocessor 306 begins to count. Simultaneously microprocessor 306 sends an ON-signal to X-ray tube controller 114 which turns on X-ray tube 33, which will operate at the operating current, focal spot size and voltage settings provided by indicators 303 and 304. Radiation begins to be delivered to the patient who is positioned in the X-ray machine, as shown in FIG. 5 for example. Sensor 27 begins to detect radiation passing through tissue and sends current to amplifier integrator 327 proportional to the radiation intensity which it receives. The output of amplifier integrator 327 to microprocessor 306 begins at a nominal zero-volt setting when the X-ray beam is turned on and increases as current from sensor 27 is integrated. Sensor 28 begins detecting radiation not passing through tissue and sending current to integrator 328 which sends an integrated signal to microprocessor 306.

At the end of the sampling time for which sampling timer 326 is set, microprocessor 306 reads tissue thickness x from indicator 302, initial current, focal spot size and initial voltage from indicators 303 and 304, source-to sensor distance D27 from indicator 307, source-to-sensor distance D28 from indicator 308, and integrated voltages from integrators 327 and 328. From $\mu$-table 316 microprocessor 306 determines the attenuation coefficient of the tissue being exposed. Using this attenuation coefficient and again using the tissue thickness provided by indicator 302, microprocessor 306 determines optimum voltage, focal spot size and current. Comparing these calculated values to the initial values microprocessor 306 determines whether voltage, current, and focal spot size should be increased or decreased and by how many steps. Microprocessor 306 then sends signals to X-ray tube controller 114 indicating how many steps to increase or decrease the current, focal spot size and voltage, sends signals to initial current, focal spot size and voltage indicators 303 and 304 establishing these optimum values as the initial values for the next exposure. Microprocessor 306 also provides appropriate voltage, current and focal spot size signals to front panel 314 so these values become displayed on front panel 314. When X-ray tube controller 114 receives signals to increase or decrease voltage, current, and/or focal spot size it adjusts X-ray tube 33 accordingly so that for the remainder of the exposure X-ray tube 33 is operating at optimum values. Microprocessor 306 continues to send the ON signal to X-ray tube controller 114 and to front panel 314 until integrator signal 327, calibrated by optical density selector signal 305 from front panel 314 or by a density selector switch which calibrates integrator 327 reaches an appropriate integrated value, at which time microprocessor 306 sends OFF signals to X-ray tube controller 114 and front panel 314. The X-ray tube 33 turns off and the exposure is complete. Film in film screen cassette 24 (FIG. 5) is properly exposed and ready for development.

Signal line 315 from display panel 314 to X-ray controller 114 supplies additional control signals such as table tilting, table positioning, film position, collimator control, and tube safety cut-off controls.

FIG. 12 also shows source to tissue distance indicator 330 which indicates the distance from X-ray source 11 to the top surface of the tissue, in FIG. 5 the top surface of compressed breast 22. Using the calculated optimum current, and voltage and the source-to-tissue distance from indicator 330, and the total exposure time, microprocessor 306 calculates the total radiation dosage to the near surface of patient tissue and sends this dosage value to front panel 314 which displays it. Total exposure time may be provided by having sampling timer 326 continue to count through the entire exposure or by providing a separate exposure time counter. The formula for exposure is $$E = k' V^2 i_{33} t / D_{22}^2 \quad (20)$$

where
E is exposure to the near surface tissue
k' is a proportionality constant
V is machine operating voltage
$i_{33}$ is current to X-ray tube 33
t is exposure time
$D_{22}$ is distance from source 11 to the near surface of tissue 22

The microprocessor can of course also be programmed to calculate dosage to the midpoint of the tissue or average dosage to the glandular tissue or to the lower surface or average dosage to glandular tissue, but such a calculation must also take into account the attenuation of radiation by the tissue as well as the increase in distance, radiation back scatter from objects beneath the tissue and exposure-to-dosage conversion factors for the appropriate tissue as a function of voltage.

The embodiment of FIG. 12 uses two sensors and determines tissue attenuation coefficient as a function of the ratio of current through sensors 27 and 28. An embodiment similar to FIG. 12 which uses a single sensor would have a different μ-table from μ-table 316. Rather than comparing the integrated signal from integrator 327 to the integrated signal from integrator 328, a single sensor model would compare a single signal integrated from a sensor such as sensor 26 in FIG. 6 to a value for the appropriate voltage taken from a set of values obtained over a range of voltages using sensor 26 while the machine was being operated for calibration purposes with no tissue present.

Several embodiments of the current invention have been described here. This disclosure is meant to be exemplary and not limiting. In light of this disclosure other embodiments will become apparent to those skilled in the art.

I claim:
1. An X-ray apparatus comprising
an X-ray tube having a cathode which emits electrons and an anode on which said electrons impinge and which is a source of X-rays, said tube having an operating voltage which is the voltage drop between said anode and said cathode, a tube current which is the current between said anode and said cathode, and a focal spot size which is the area of said anode on which said electrons impinge, and in which said voltage, said current and said current and said focal spot size have initial settings;
a collimator having an opening through which said X-rays leaving said source in the direction of said opening may pass;
means for holding tissue to be examined in position for being irradiated;
means for showing an image of X-rays which have passed through said tissue;
at least one sensor which generates sensor signals for detecting radiation passed through said tissue and through said means for showing an image, and for calibrating said X-ray apparatus; and
means for receiving said sensor signals from said at least one sensor and based on said sensor signals sending control signals which control said operating voltage, said tube current, and said focal spot size.

2. An X-ray apparatus as in claim 1 in which said at least one sensor is two sensors, a first sensor located to detect radiation passed through said tissue and a second sensor located to detect radiation not passed through said tissue for calibrating said X-ray apparatus, and in which said means for receiving is a microprocessor which determines a tissue attenuation coefficient using said sensor signals from said first and second sensors.

3. An X-ray apparatus as in claim 1 in which said means for receiving comprises:
a microprocessor which determines tissue attenuation coefficient and based on said coefficient sends signals which cause said operating voltage, said tube current, and said focal spot size to increase, decrease, or remain unchanged.

4. An X-ray apparatus as in claim 2 in which said microprocessor comprises means for determining maximum radiation dosage, midpoint dosage to said tissue, and average dosage of glandular tissue accumulated during an exposure, and displaying said radiation dosages on a display panel.

5. An X-ray apparatus as in claim 1 in which said at least one sensor is one sensor located to detect radiation passed through said tissue, and usable when said tissue is not present for calibrating said X-ray apparatus, and in which said means for receiving includes an integrator, a calibration signal source, and a comparator, and in which said comparator serves to
cause said operating voltage to increase when the output of said integrator is less than the output of said calibration signal source by a first selected amount;

cause said operating voltage to decrease when the output of said integrator is more than the output of said calibration signal source by a second selected amount;

cause both said operating voltage and said focal spot size to increase when the output of said integrator is less than the output of said calibration signal source by a third selected amount larger than said first selected amount; and cause both said operating voltage and said focal spot size to decrease when the output of said integrator is more than the output of said calibration signal source by a fourth selected amount larger than said second selected amount.

6. An X-ray apparatus as in claim 5 in which said means for receiving further comprises:

an adaptor/interface which receives signals from said comparator and based on said signals from said comparator sends signals to a controller of said X-ray tube causing said controller to increase, decrease or not change said voltage, tube current, and focal spot size of said X-ray tube.

7. An X-ray apparatus as in claim 1 in which said at least one sensor is one sensor located to detect radiation passed through said tissue, and used when said tissue is not present for calibrating said X-ray apparatus, and in which said means for receiving is a microprocessor which calculates a calibration coefficient using calibration signals from said one sensor taken while operating said X-ray apparatus when said tissue is not present, and calculates a tissue absorption coefficient using said calibration coefficient and exposure signals taken from said one sensor while operating said X-ray apparatus when said tissue is present.

8. An X-ray apparatus as in claim 7 in which said microprocessor further comprises a table of optimum operating voltage and optimum focal spot size and current as a function of tissue absorption coefficient, and said microprocessor sends signals causing said X-ray tube to operate at said optimum operating voltage and said optimum focal spot size and current.

9. An X-ray apparatus as in claim 7 in which said microprocessor further controls exposure time.

10. An X-ray apparatus as in claim 7 further comprising a thickness sensor for sensing thickness of said tissue and in which said microprocessor receives signals from said thickness sensor and uses said signals from said thickness sensor to calculate said optimum voltage, current and focal spot size.

11. An X-ray apparatus as in claim 1 in which said at least one sensor is at least one scintillation counter.

12. An X-ray apparatus as in claim 1 in which said at least one sensor is at least one semiconductor.

13. An X-ray apparatus as in claim 12 in which said semiconductor is a photodiode.

14. An X-ray apparatus as in claim 1 in which said tissue is breast tissue and said image is a mammogram.

15. An X-ray apparatus as in claim 1 in which said initial settings are average settings for the type of tissue being exposed.

16. An X-ray apparatus as in claim 1 where said initial settings are optimal settings of the previous exposure.

17. An X-ray apparatus as in claim 1 in which said means for showing said image is photosensitive film.

18. An X-ray apparatus as in claim 17 in which said photosensitive film is adjacent to a film screen sensitive to X-ray photons.

19. An X-ray apparatus as in claim 1 in which said means for showing said image is a fluoroscope.

20. An X-ray apparatus as in claim 1 in which said means for showing said image is an electrostatically printed page.

21. An X-ray apparatus as in claim 1 in which said means for showing said image is a recording on a digital recording means.

22. An X-ray apparatus as in claim 1 in which said means for showing an image of X-rays which have passed through said tissue includes a grid device, a film screen cassette, a breast tray, and an X-ray film.

23. An X-ray apparatus as in claim 1 further comprising a front panel on which are displayed said optimum values of current, voltage, and focal spot size.

24. A method for optimizing an X-ray image from an X-ray apparatus comprising an X-ray tube having a cathode which emits electrons and an anode on which said electrons impinge and which is a source of X-rays, said tube having an operating voltage which is the voltage drop between said anode and said cathode, a tube current which is the current between said anode and said cathode, and a focal spot size which is the area of said anode on which said electrons impinge, and in which said voltage, said current and said focal spot size have initial settings;

a collimator having an opening through which said X-rays leaving said source in the direction of said opening may pass;

means for holding tissue to be examined in position for being irradiated;

means for showing an image of X-rays which have passed through said tissue;

at least one sensor which generates sensor signals for detecting radiation passed through said tissue and through said means for showing an image, and for calibrating said X-ray apparatus; and means for receiving said sensor signals from said at least one sensor and based on said sensor signals sending control signals which control said operating voltage, said tube current, and said focal spot size; comprising the steps of:

positioning said tissue;

determining thickness of said tissue and providing said tissue thickness to said microprocssor;

operating said X-ray apparatus at said initial settings;

in a sampling time small in comparison to an expected total exposure time calculating optimum voltage, current and focal spot size settings for the tissue being exposed;

at the end of said small sampling time changing voltage, current and focal spot size settings to said optimum voltage, current and focal spot size settings for the tissue being exposed; and continuing to operate said X-ray apparatus at said optimal settings until an optimum visualization of said means for showing an image is achieved.

25. A method as in claim 24 where said tissue comprises breast tissue, said means for holding comprises breast compression plates, and said determining tissue thickness comprises determining separation between said breast compression plates.

26. A method as in claim 24 further comprising the step of calibrating said sensors before positioning said tissue.

27. A method as in claim 26 further comprising additional calibration in the form of providing information from a second sensor during exposure.

28. A method for optimizing an X-ray image from an X-ray apparatus as in claim 24 wherein said at least one sensor is one sensor and said step of calculating optimum voltage, current and focal spot size for the tissue being exposed comprises:

before said step of positioning said tissue, operating said X-ray apparatus at said initial settings, and determining current through said one sensor when said tissue to be examined is not in position for being irradiated;

determining thickness of said tissue to be examined in position for being irradiated;

determining current through said one sensor when said tissue to be examined is being irradiated;

calculating a tissue absorption coefficient as $$\mu = \frac{\ln i_{cal} - \ln i_{exp} + 2 \ln D_{cal} - 2 \ln D_{exp}}{x}$$

where $\mu$ is absorption coefficient of said tissue, $i_{cal}$ is said current through said one sensor when said tissue is not in position for being irradiated, $i_{exp}$ is said current through said one sensor when said tissue is being irradiated, $x$ is thickness of said tissue to be examined in position for being irradiated, $D_{cal}$ is distance from source to sensor when said tissue is not in position for being irradiated, and $D_{exp}$ is distance from source to sensor when said tissue is being irradiated; and determining said optimum voltage, current, and focal spot size as a function of said absorption coefficient and said initial settings of voltage, current, and focal spot size.

29. A method for optimizing an X-ray image from an X-ray apparatus as in claim 28 wherein said means for receiving said sensor signals comprises a microprocessor and said step of determining said optimum voltage, current, and focal spot size as a function of said absorption coefficient and said initial settings of voltage, current and focal spot size comprises reading said optimum voltage, current, and focal spot size from a table stored in said microprocessor.

30. A method for optimizing an X-ray image from an X-ray apparatus as in claim 22 wherein said at least one sensor is two sensors, a first sensor located in the path of X-rays which have passed through said tissue and through said means for showing an image, and a second sensor located in the path of X-rays which have not passed through said tissue, and said step of calculating optimum voltage, current and focal spot size settings for the tissue being exposed comprises:

before positioning said tissue but after locating said means for producing an image, said first sensor, and said second sensor.

determining a normalization factor N between said first and second sensors by operating said X-ray apparatus and measuring current through said first sensor $iN_1$, current through said second sensor $iN_2$, distance from said X-ray source to said first sensor $DN_1$, and distance from said X-ray source to said second sensor $DN_2$, and calculating $N = iN_1 DN_1^2 / iN_2 DN_2^2$;

then before a particular exposure of said tissue, determining distance $D_1$ from said source of X-rays to said first sensor;

determining distance $D_2$ from said source of X-rays to said second sensor;

after said positioning said tissue, said determining said thickness $x$, and said operating said X-ray apparatus at said initial settings in said sampling time small compared to said expected total exposure time, determining current through said first sensor $i_1$, and current through said second sensor $i_2$;

calculating a tissue absorption coefficient as $$\mu = \frac{N + 2 \ln D_2 + \ln i_2 - 2 \ln D_1 - \ln i_1}{x}$$

and determining said optimum voltage, current, and focal spot size as a function of said absorption coefficient and said initial settings of voltage, current, and focal spot size.

31. A method for optimizing an X-ray image from an X-ray apparatus as in claim 30 wherein said means for receiving said sensor signals comprises a microprocessor and said step of determining said optimum voltage, current, and focal spot size as a function of said absorption coefficient and said initial settings of voltage, current and focal spot size comprises reading said optimum voltage, current, and focal spot size from a table stored in said microprocessor.

32. A method for optimizing an X-ray image as in claim 24 in which said step of calculating optimum voltage produces a voltage calculation to the nearest 1 kV.

33. A method for optimizing an X-ray image as in claim 24 comprising the further step of displaying said optimum voltage, current, and focal spot size on a panel.

34. An X-ray apparatus comprising an X-ray tube having a cathode which emits electrons and an anode on which said electrons impinge and which is a source of X-rays, said tube having an operating voltage which is the voltage drop between said anode and said cathode, a tube current which is the current between said anode and said cathode, and a focal spot size which is the area of said anode on which said electrons impinge, and in which said voltage, said current and said focal spot size having initial settings;

a collimator having an opening through which said X-rays leaving said source in the direction of said opening may pass;

means for holding an object to be examined in position for being irradiated;

means for showing an image of X-rays which have passed through said object;

at least one sensor which generates sensor signals for detecting radiation passed through said object and through said means for showing an image, and for calibrating said X-ray apparatus; and means for receiving said sensor signals from said at least one sensor and based on said sensor signals sending control signals which control said operating voltage, said tube current, and said focal spot size.

* * * * *

UNITED STATES PATENT AND TRADEMARK OFFICE
CERTIFICATE OF CORRECTION

PATENT NO. : 4,763,343

DATED : August 9, 1988

INVENTOR(S) : Nicola E. Yanaki

It is certified that error appears in the above-identified patent and that said Letters Patent is hereby corrected as shown below:

```
Col. 8, line 43, change "opening angle a." to --opening
                angle A.--.

Col. 20, line 18, delete "and said current".

Col. 23, line 52, change "claim 22" to --claim 24--.

Col. 23, line 62, change "sensor." to --sensor,--.
```

Signed and Sealed this

Ninth Day of May, 1989

*Attest:*

DONALD J. QUIGG

*Attesting Officer*  *Commissioner of Patents and Trademarks*